(12) United States Patent
Dehdashtian et al.

(10) Patent No.: US 6,375,675 B2
(45) Date of Patent: Apr. 23, 2002

(54) METHODS AND APPARATUS FOR INTRALUMINAL PLACEMENT OF A BIFURCATED INTRALUMINAL GRAFT

(75) Inventors: Mark Dehdashtian, Costa Mesa, CA (US); Geoffrey H. White, East Balmain; Weiyun Yu, Birchgrove, both of (AU)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

(21) Appl. No.: 09/819,454

(22) Filed: Mar. 27, 2001

Related U.S. Application Data

(60) Division of application No. 09/204,699, filed on Dec. 3, 1998, which is a continuation-in-part of application No. 09/163,580, filed on Sep. 30, 1998, now abandoned.

(51) Int. Cl.[7] ................................................. A61F 2/06
(52) U.S. Cl. ...................................... 623/1.13; 623/1.16
(58) Field of Search .............................. 623/1.13, 1.14, 623/1.16, 1.35, 1.34

(56) References Cited

U.S. PATENT DOCUMENTS

| | | | | |
|---|---|---|---|---|
| 5,064,435 A | * | 11/1991 | Porter | 623/1 |
| 5,676,697 A | * | 10/1997 | McDonald | 623/1.35 |
| 5,693,088 A | * | 12/1997 | Lazarus | 623/1 |
| 5,824,037 A | * | 10/1998 | Fogarty et al. | 623/1 |
| 5,843,160 A | * | 12/1998 | Rhodes | 623/1 |
| 6,099,558 A | * | 8/2000 | White et al. | 623/1.16 |

* cited by examiner

Primary Examiner—Cary E. O'Connor
(74) Attorney, Agent, or Firm—Vascular Therapies; Bruce M. Canter; Peter Jon Gluck

(57) ABSTRACT

Methods and apparatus for placing a bifurcated aortic graft, with extensions, into a body lumen. An aortic graft is provided with a unique combination of self-expanding a balloon expandable wires. The aortic graft is bifurcated and includes ipsilateral and contralateral legs. Two extension grafts are provided for frictional engagement with the legs of the aortic graft. For placement of the bifurcated aortic graft with extensions, an introducer assembly including a dilator and a sheath assembly provides access for the introduction of a main catheter and a directional catheter. The main catheter is provided for deployment of the bifurcated aortic graft within the lumen of a vessel. A balloon is provided on the main catheter for expanding the balloon-expandable wires of the aortic graft. The directional catheter, which includes a deflecting spring portion, permits placement of a guidewire through the ipsilateral leg and into the contralateral leg of the aortic graft. In turn, a second introducer sheath and a second catheter assembly are provided contralaterally for introduction of a graft extension. Upon balloon-expansion, the graft extension is frictionally engaged with the contralateral leg of the aortic graft. A third catheter assembly including a second extension graft is provided for introduction of the extension graft and balloon-expansion thereof for frictional engagement with the ipsilateral leg of the graft.

25 Claims, 31 Drawing Sheets

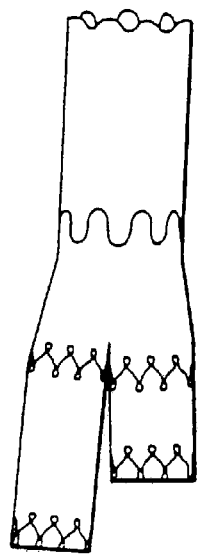 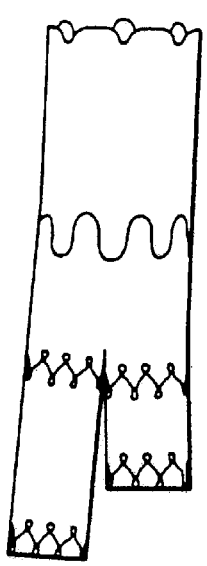 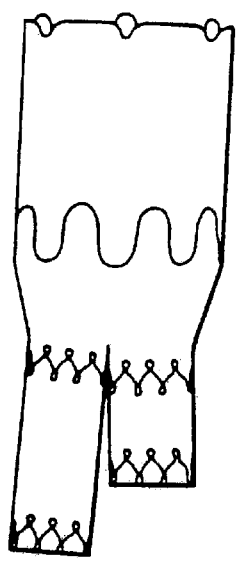
FIG. 2B   FIG. 2C   FIG. 2D
  
FIG. 2E   FIG. 2F   FIG. 2G

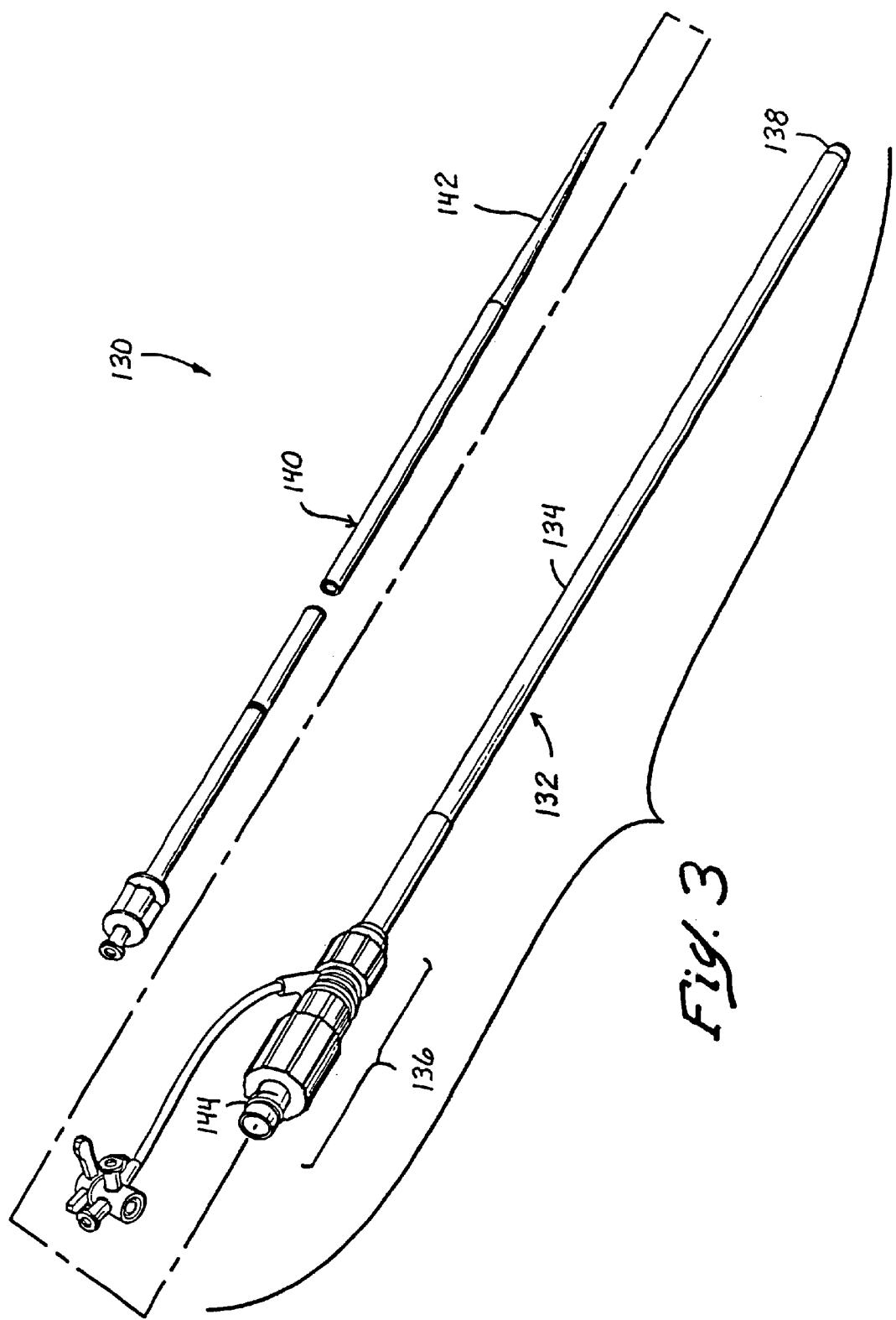

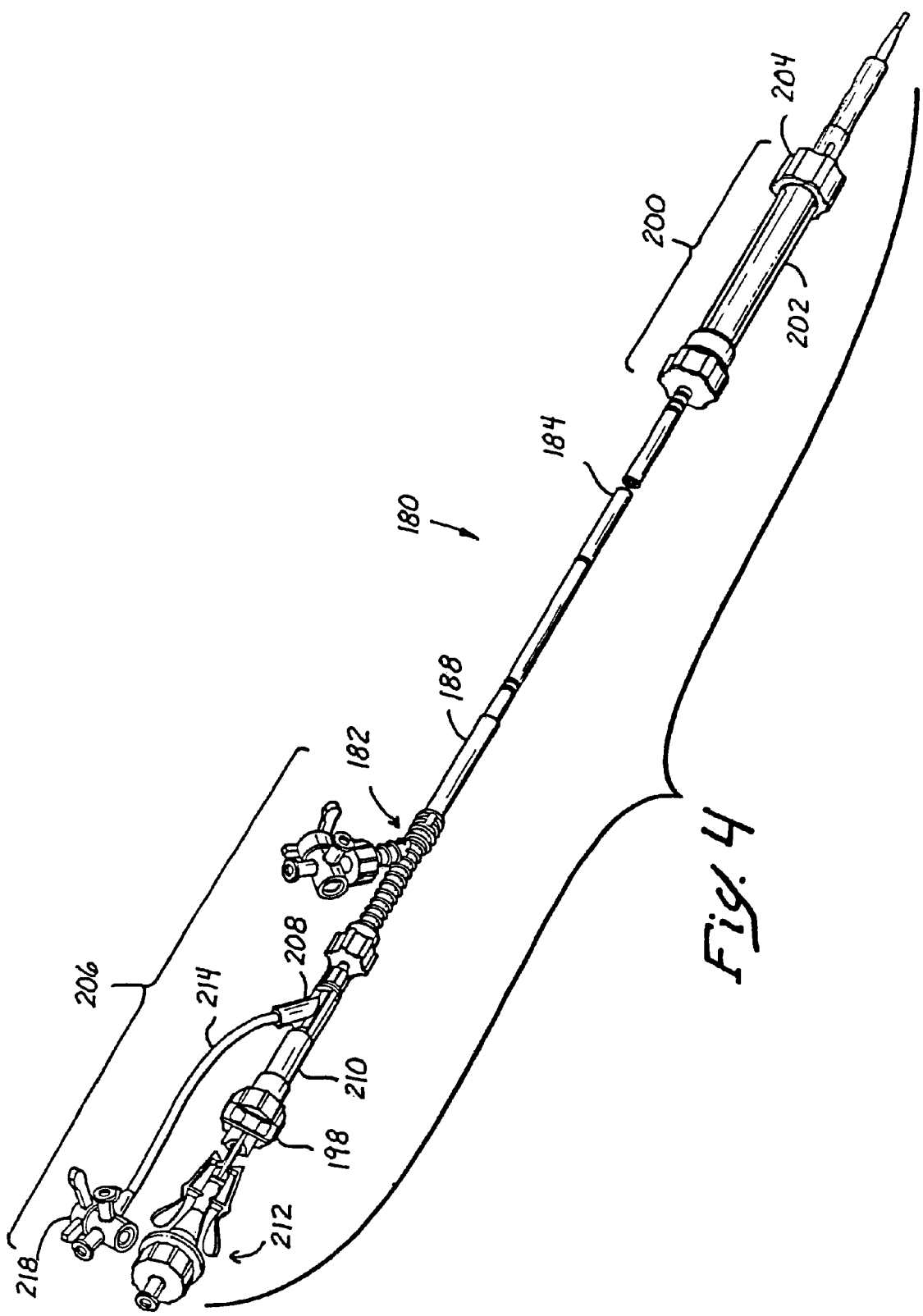

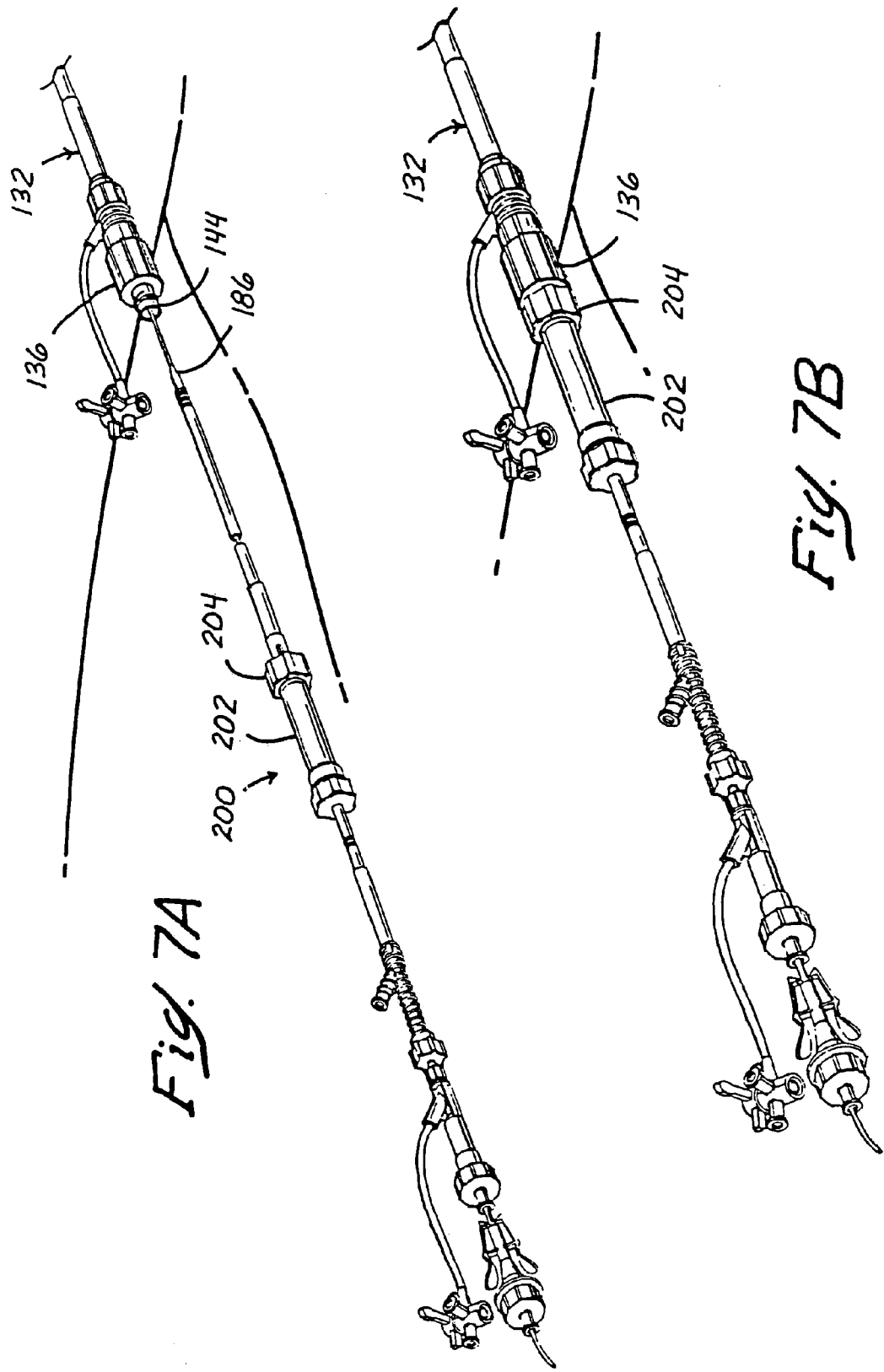

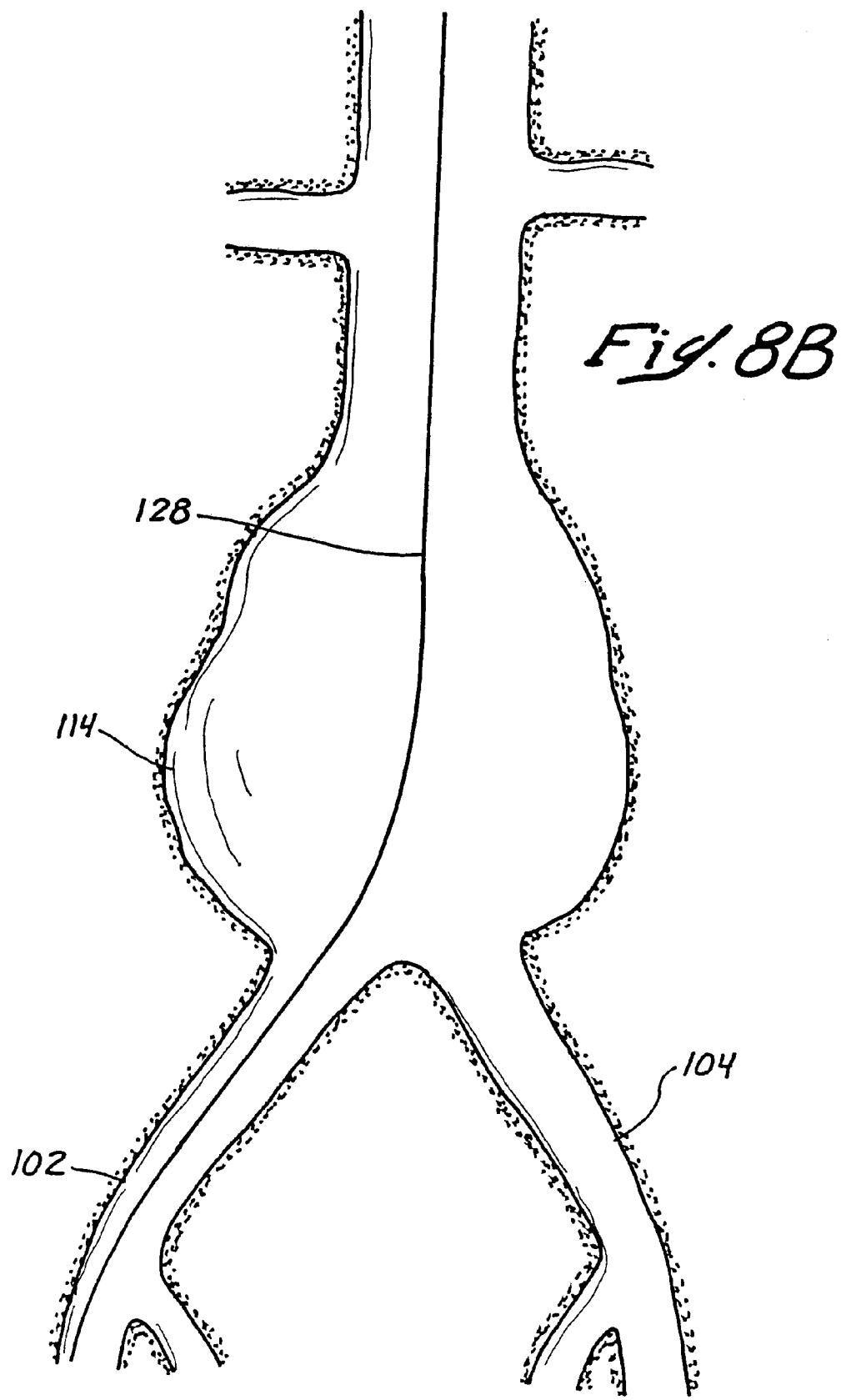

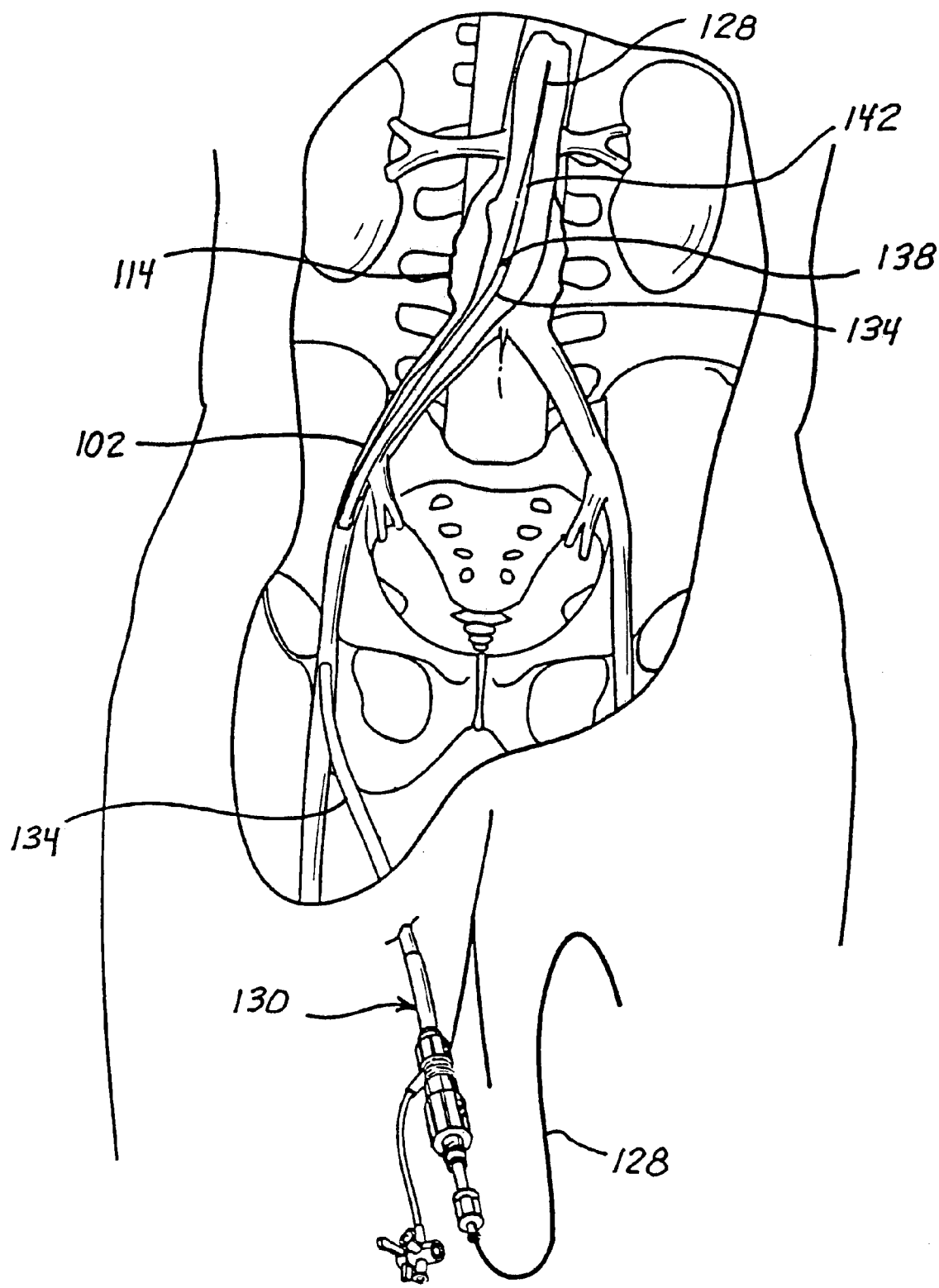

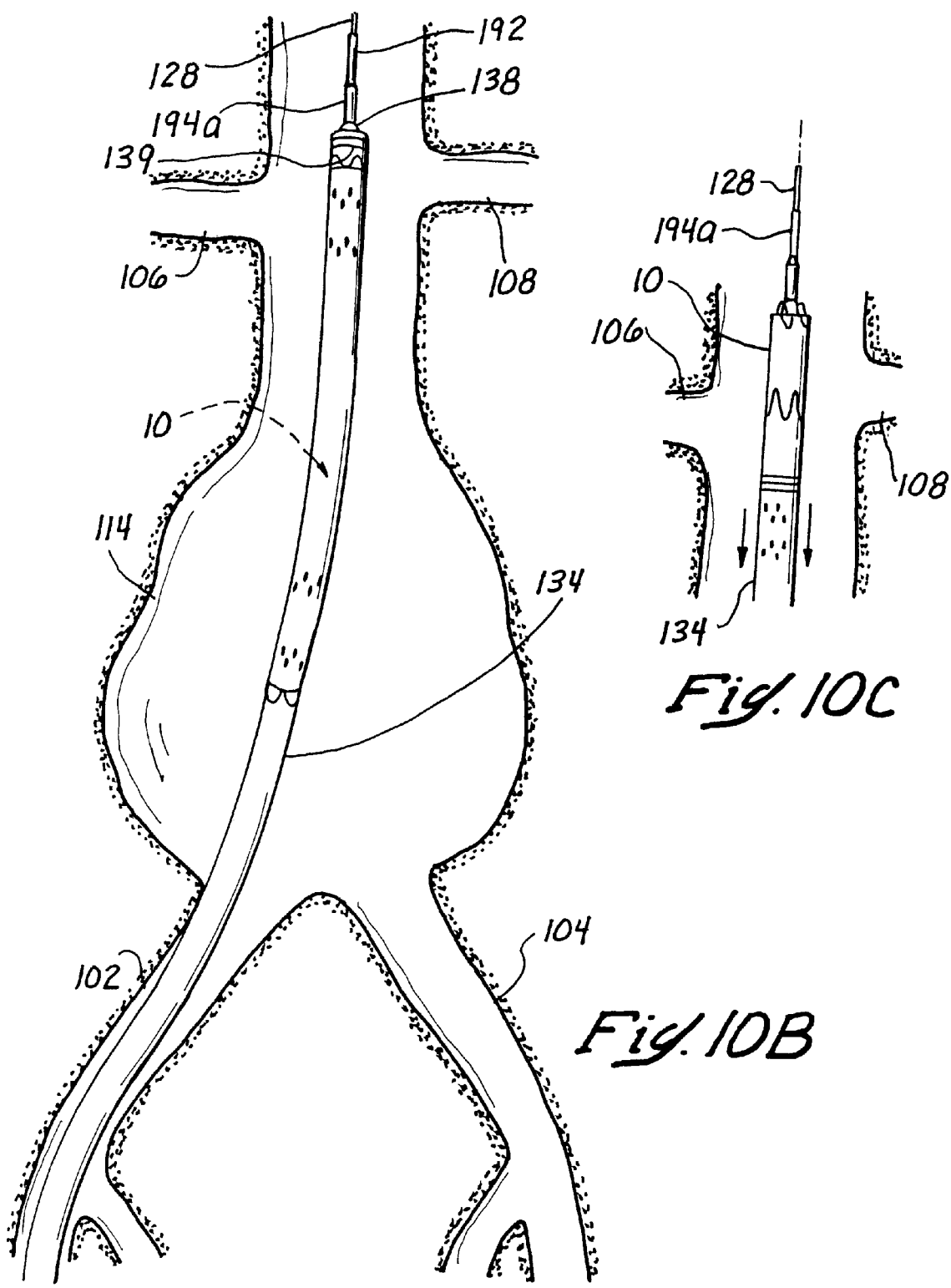

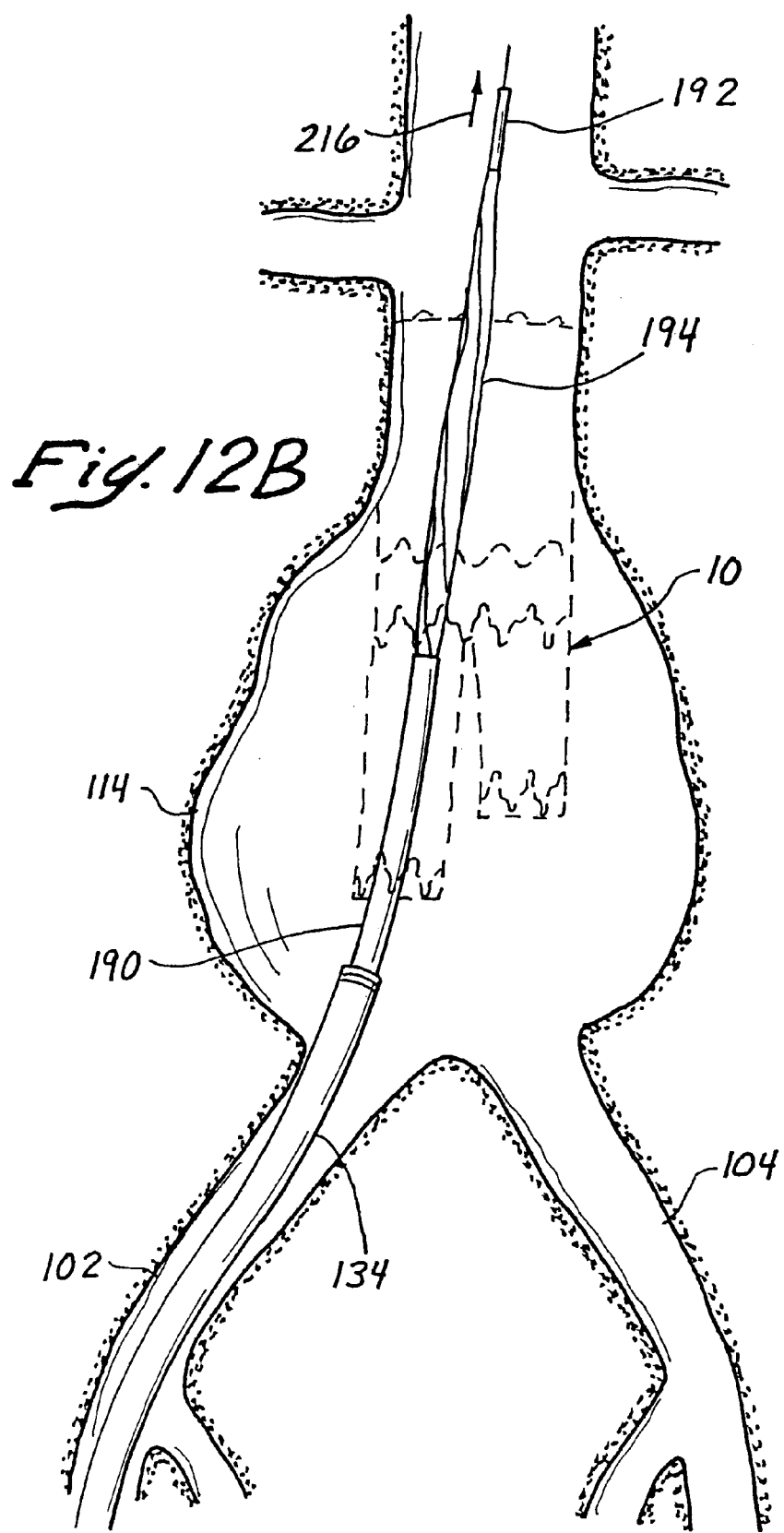

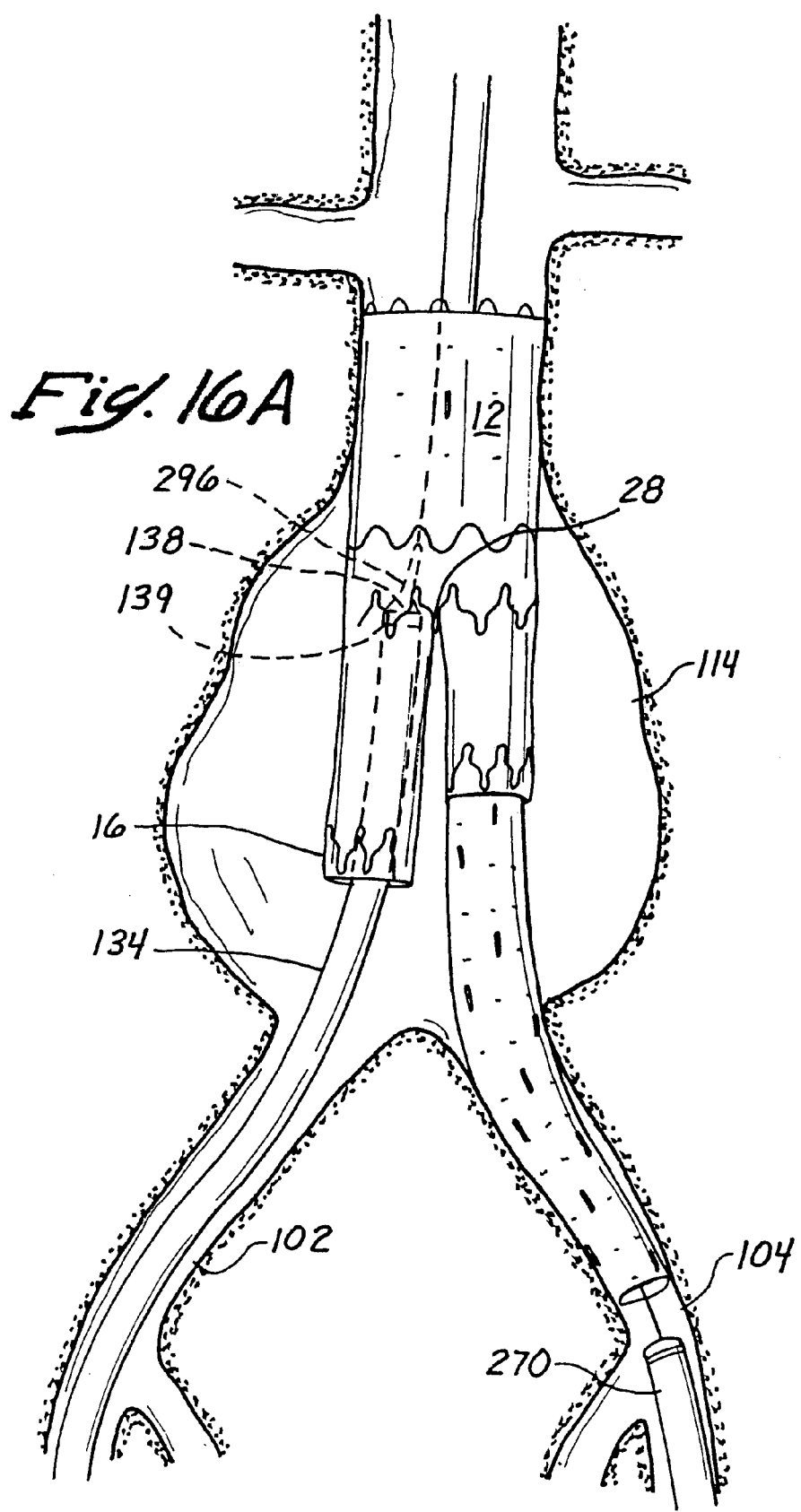

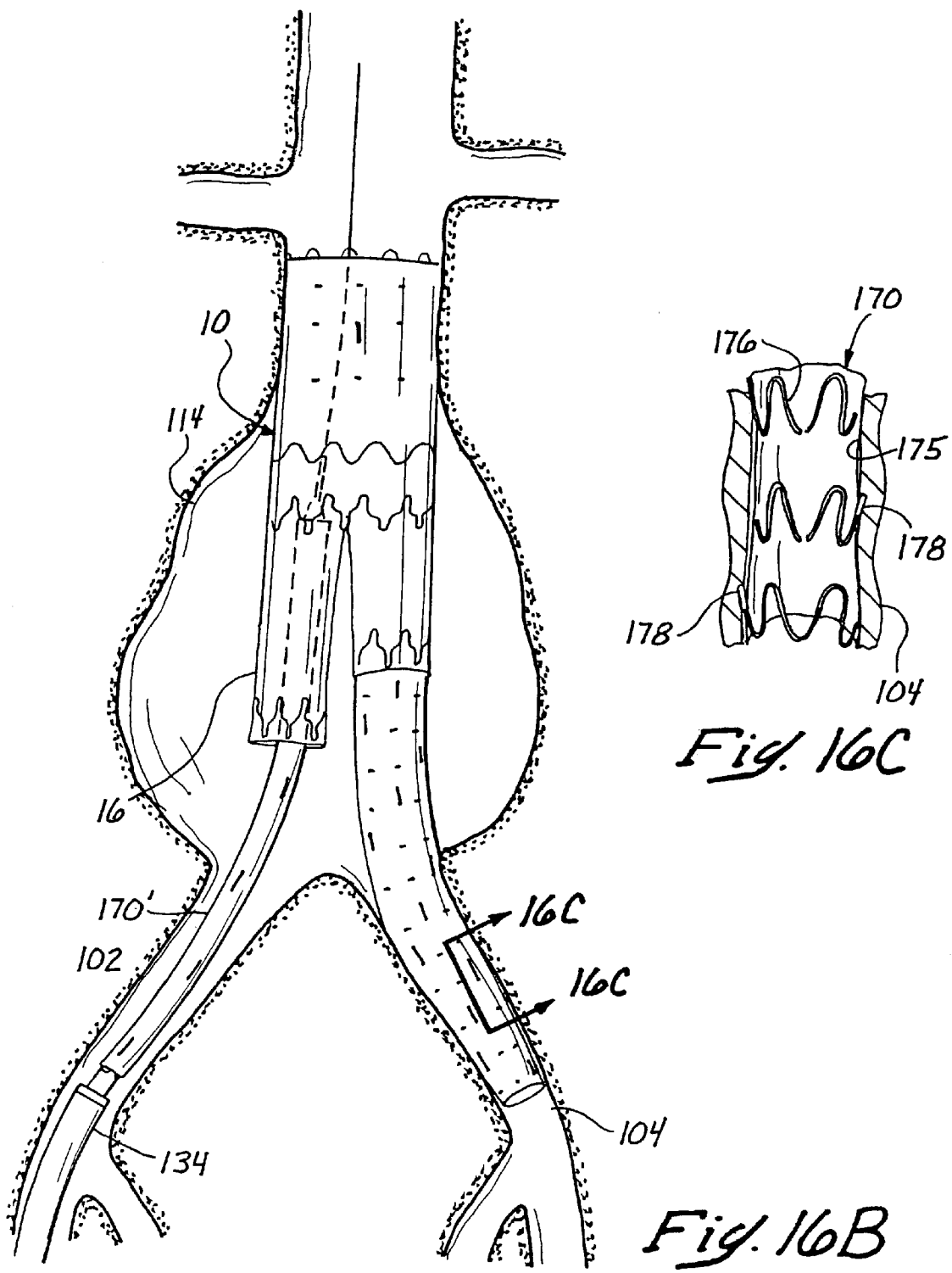

METHODS AND APPARATUS FOR INTRALUMINAL PLACEMENT OF A BIFURCATED INTRALUMINAL GRAFT

The present application is a divisional patent application of U.S. application Ser. No. 09/204,699, filed Dec. 3, 1998, pending, which is a continuation-in-part application of U.S. application Ser. No. 09/163,580, filed Sep. 30, 1998, abandonded.

BACKGROUND OF THE INVENTION

1. Field of the Invention

The present invention is directed generally to methods and apparatus for positioning an intraluminal graft. More specifically the present invention is related to methods and apparatus for positioning an intraluminal graft into a bifurcating vessel such as an artery.

2. Discussion of Related Technology

An artery or other vessel that is weakened by disease, injury, or congenital defect, can become distended due to the pressure of blood or other fluid flowing-through the weakened area. In the vasculature, this distended weakening is called an aneurysm. An aneurysm typically occurs in the arterial vessels of the head, chest, or abdomen. The distension may cause the vessel to rupture, which can have serious, even life-threatening consequences.

Aneurysms in the abdominal aorta are typically distended around the circumference of the aorta and tapered at both ends. Most aneurysms of the abdominal aorta are caused by atherosclerotic weakening of a segment of the wall. Abdominal aneurysms may cause backache and severe pain, and may be visible as a throbbing swelling. If an abdominal aorta ruptures, it is seriously life threatening.

Traditionally, aneurysms have been treated by radical surgical graft replacement. This approach is risky for the patient and is sometimes not feasible due to other preexisting disease states of the patient. More recently, aneurysms have been treated by placement of an intraluminal or endovascular graft. These intraluminal or endovascular grafts may be of various types, including grafts having stents, wireforms, or other attachment means attached to or integrated into the graft structure.

In general, intraluminal grafts and their respective support and/or attachment means fall into two major categories, self-expanding and pressure expandable. Self-expanding intraluminal grafts, are supported and/or attached via resilient or shape-memory material such as spring steel or Nitinol™. Self-expanding material is capable of being formed in a configuration from which it may be compressed to a radially compact diameter for placement within a damaged vessel. At the time of use, the memory feature of the-se materials causes them to self-expand from the radially compact diameter to the expanded operative diameter.

Pressure-expandable intraluminal grafts are supported and/or attached via plastically deformable material such as stainless steel that is initially formed in its radially compact diameter. This type of material does not have memory, and will remain in the radially compact diameter until manually expanded. Typically, outwardly directed pressure is exerted upon the graft through use of a balloon so as to cause radial expansion and resultant plastic deformation of the material to its operative diameter.

Careful positioning and firm implantation of the intraluminal graft is critical to the successful treatment of the underlying medical condition. This is particularly difficult to accomplish when the aneurysm extends from an artery into one or more divergent arteries. A "trouser graft" has been suggested for use in a first main artery and a pair of divergent arteries by White et al. in PCT Application Nos. WO 97/17910; WO 97/17911; WO 97/18006; WO 97/26936; and WO 97/26938; all of which are hereby incorporated herein by reference in their entireties. A trouser graft comprises a first tubular body that bifurcates into two smaller tubular bodies. In the referenced disclosures, the first tubular body is placed in first artery and the two smaller tubular bodies are placed so as to extend within the two divergent arteries.

Notwithstanding the important teachings of the foregoing references, features of the aforementioned device have recognized shortcomings that make them less than complete solutions to the treatment of aneurysms in the vasculature, or to the treatment of similar damage to other vessels. The present invention provides substantial improvements to the methods and apparatus of the prior art.

SUMMARY OF THE INVENTION

It is an object of the present invention to provide an improved intraluminal graft and method for placement of same that diminishes deleterious kinking and twisting of the graft during and after placement thereof in a vessel.

It is another object of the present invention to provide an improved intraluminal graft and method for placement of same that provides control over inadvertent longitudinal movement within a vessel.

Another object of the present invention is to provide an improved intraluminal "trouser" graft and method for placement of same that precludes inadvertent separation of the legs of the trouser.

These and other objects and features of the present invention will become more fully apparent from the following description and appended claims, or may be learned by the practice of the invention as set forth hereinafter.

To achieve the forgoing objects, and in accordance with the invention as embodied and broadly described herein, the present invention relates to new and useful apparatus and methods for placing a bifurcated graft at the site of a damaged vessel. In a preferred embodiment, the methods and apparatus of the present invention are directed to placement of a bifurcated graft within an aneurysm located in the abdominal aorta downstream of the renal arteries. Preferably, placement of the graft is through the right femoral artery of a patient.

An introducer assembly is provided which is configured for placement over a guidewire and for facilitating the advancement of various catheter assemblies required in connection with the practice of the invention. The introducer assembly includes a sheath, valve head, and a dilator. The sheath is preferably cylindrical in shape and is formed so as to have an appropriate flexibility and an outer diameter suitable for placement at the location of an aneurysm to be repaired. The valve head permits insertion and removal of various catheters during the method of the present invention without significant loss of blood from the femoral artery. The proximal end of the valve head is provided with a threaded connector which facilitates connection of the valve head to other catheters. The dilator, which includes a tapered tip, is placed during use through the valve head and the sheath so that the tapered tip portion protrudes from the sheath. The dilator tip portion is capable of being advanced gently through the tortuous pathway of the vasculature without causing undue trauma or a perforation, yet is also sufficiently stiff to cause the blood vessels to assume a less tortuous path.

Another component of the present invention is a bifurcated aortic graft. The preferred bifurcated aortic graft includes both self-expanding and balloon-expandable wireforms along its length. The balloon-expandable wires permit precision in placement of the aortic graft. The self-expanding wires open within the vessel immediately upon deployment from the main catheter assembly, which allows insertion of other modular components, opens a removal path for the inflatable balloons, and reduces kinking. The self-expanding wires also increase the anchoring force between the bifurcated graft and modular extension grafts used to extend the bifurcated graft into communication with non-distended vessel walls.

One of the self-expanding wireforms is located at a septum region of the bifurcated graft. The septum region separates an ipsilateral leg from a contralateral leg ("ipsilateral" and "contralateral" referring to opposite lateral sides of the patient depending on the surgical approach). This septum wire prevents and helps eliminate the kinks that are typically encountered with conventional bifurcated grafts. In addition, the self-expanding wireform at the septum region includes crimps functioning as radiopaque markers generally pointing to the septum region, which aids in identifying the location of the septum under fluoroscopy. Two additional self-expanding wireforms are located at the ends of each leg Of the bifurcated graft. These wireforms facilitate opening the legs immediately upon deployment from the main catheter assembly to allow for the insertion of modular components. These leg wireforms also contain crimps as radiopaque markers which aid in identifying the ends of the bifurcated graft legs. All crimps on the self-expanding wireforms are placed on the anterior side of the graft, thus aiding in orientation of the graft under fluoroscopy.

The main catheter assembly is utilized to place the aortic graft described above, which is compressed and loaded onto the distal end of the main catheter assembly. The main catheter assembly is sized such that it will fit inside the introducer sheath.

The components of the main catheter assembly include the following: a rigid loader configured for connection to the valve head of the sheath assembly; a proximal connector assembly including a distal pusher connector; an elongate, tubular pusher body; an elongate catheter with a coaxial tube construction; and an inflatable catheter balloon.

In addition to the aortic graft, two additional graft portions are adapted to extend into the respective iliac arteries to form a frictional engagement with the ipsilateral and contralateral legs of the aortic graft. These extension grafts typically comprise straight cylindrical tubes, with an upstream end having a common diameter. The upstream ends interlock with the respective downstream portions of the aortic graft.

The present invention may further include a directional catheter which permits placement of the graft extensions. The directional catheter includes a deflecting spring portion, a knob used to deflect the spring portion, and a connector nut for connection with the sheath assembly.

The preferred method for using the aforementioned components of the present invention includes the following steps. An incision is made and a primary guidewire is placed in conventional fashion in the ipsilateral side, that is, for example, through the right femoral artery and the right common iliac artery so as to extend well upstream of the aneurysm. The introducer assembly is advanced over and along the primary guidewire into a position upstream of the renal arteries. Once the sheath of the introducer assembly has been properly placed, the dilator is retracted along the guidewire and then completely removed from within the sheath assembly and from primary guidewire. The main catheter assembly is inserted over the primary guidewire and into the sheath assembly, and then connected thereto. The pusher body is distally advanced to push the aortic graft and main catheter through to the end of the introducer sheath. The sheath containing the aortic graft is then retracted slowly to approximately a desired deployment position in the abdominal aorta. The introducer sheath is then retracted to a position just below the septum region, freeing the aortic graft and exposing it to blood flow.

The balloon-expandable, upstream portion of the aortic graft remains in a substantially compressed configuration. The catheter balloon is inflated which facilitates the concurrent radial expansion of the balloon-expandable portions of the graft from the initial, collapsed orientation, to the second, expanded orientation. In one embodiment of the present invention, the graft is slightly over-sized to optimize engagement of the aortic graft with the aortic wall. When the graft is fully expanded, the upstream end thereof frictionally engages the luminal surfaces of unaffected regions of the aorta just below the renal arteries. After the graft has been radially expanded in the aforementioned manner, the balloon is deflated, longitudinally stretched to prevent snagging on the graft, and then removed. The main catheter is then withdrawn slowly and carefully, with the introducer sheath and the primary guidewire remaining in place.

For placement of the graft extensions, the directional catheter is first inserted over the primary guidewire through the ipsilateral side, that is, for example, through the right femoral artery and the right common iliac artery. The spring portion of the directional catheter is positioned such that it is above the septal region of the aortic graft. The spring portion is; deflected by pulling proximally on the knob. A supplemental guidewire is then advanced through the directional catheter and out the deflected spring portion such that the supplemental guidewire extends down the contralateral leg and through the left common iliac artery. The supplemental guidewire is extended until it is in the left femoral artery, at which time the left femoral artery is cross-clamped and a cut-down or percutaneous incision is performed to retrieve the supplemental guidewire. Once the guidewire is retrieved, a stiffer guidewire is exchanged through the left femoral artery until it is within the first graft and reaches the contralateral side of the aortic graft. A second introducer assembly is then introduced over the stiff guidewire.

A second catheter assembly on which is packaged a tubular graft extension is then introduced through the second sheath assembly until the introducer sheath extends through the left iliac artery and terminates at the bifurcation point of the aortic graft. The sheath followed by the pusher of the second catheter assembly are then pulled back proximally to release the tubular graft extension. The balloon on the second catheter assembly is then inflated such that the upstream end of the extension graft is frictionally engaged with the downstream contralateral leg of the aortic graft. In one embodiment of the present invention, the extension graft is slightly over-sized such that it optimally engages with the self-expanding downstream contralateral leg. The balloon is then deflated and the second catheter assembly is removed in the manner previously described hereinabove with respect to the main catheter.

The directional catheter is also removed such that a second catheter assembly, on which is packaged a tubular graft extension, and which may be identical to the second catheter assembly, can be introduced over the primary guidewire and through the first introducer sheath assembly. This third catheter assembly is advanced until the distal end of the extension graft is at the bifurcation point of the aortic graft. In like manner to that previously described hereinabove, a third graft extension positioned on the third catheter assembly is; deployed such that its upstream end is in contact with the ipsilateral leg of the aortic graft, and its downstream end is in contact with the right iliac artery. Also in like manner to that described hereinabove, the balloon on third catheter assembly is inflated to expand the balloon expandable extension graft in the ipsilateral side. In one embodiment of the present invention, the extension graft is slightly over-sized such that it optimally engages with the self-expanding downstream ipsilateral leg. In like manner to that previously described above, the balloon is deflated, extended proximally and then the third catheter assembly is withdrawn.

In an alternate embodiment both the ipsilateral and contralateral balloon catheters could be positioned simultaneously and inflated sequentially. While maintaining the position of the third catheter balloon the second catheter balloon is deflated and stretched and the second catheter is removed. The third catheter balloon is subsequently deflated, stretched, and removed.

The second sheath assembly and the stiff guidewires are withdrawn and the contralateral incision or puncture is sutured. An angiographic examination may take place to determine if the grafts are correctly placed and functioning. The first introducer sheath assembly is withdrawn and the right femoral incision is sutured. The result is a functioning trouser graft bridging an aneurysm.

BRIEF DESCRIPTION OF THE DRAWINGS

To more fully understand the manner in which the above-recited and other advantages and objects of the invention are obtained, a more particular description of the invention will be rendered by reference to a specific embodiment thereof which is illustrated in the appended drawings. Understanding that these drawings depict only a typical embodiment of the invention and are not therefore to be considered to be limiting of its scope, the invention in its presently understood best mode for making and using the same will be described and explained with additional specificity and detail through the use of the accompanying drawings in which:

FIG. 2B is a front view of an embodiment of the aortic graft of the present invention having a tapered trunk region;

FIG. 2C is a front view of the untapered aortic graft of FIG. 1;

FIG. 2D is a front view of another embodiment of the aortic graft of the present invention having a tapered trunk region;

FIG. 2E is a front view of an embodiment of the graft extension of the present invention having a tapered downstream end;

FIG. 2F is a front view of the untapered graft extension of FIG. 2;

FIG. 2G is a front view of another embodiment of the graft extension of the present invention having a tapered downstream end;

FIG. 3 is an exploded perspective view of an introducer assembly of the present invention;

FIG. 4 is a perspective view of a main catheter assembly of the present invention;

FIG. 7A is a partial perspective view of the main catheter assembly being inserted into the introducer assembly;

FIG. 7B is a partial perspective view of the main catheter assembly connected to the introducer assembly;

FIG. 8B is a sectional view of an abdominal aorta and aneurysm ("sectional aneurysmic view") having a guidewire positioned therethrough;

FIG. 9A is a schematic abdominal view having an introducer assembly positioned therein;

FIG. 10B is a sectional aneurysmic view similar to FIG. 10A;

FIG. 10C is a detailed view of the introducer sheath being withdrawn to expose the aortic graft therein;

FIG. 12B is a sectional aneurysmic view with the deflated balloon on the main catheter assembly being stretched to facilitate removal from inside the aortic graft;

FIG. 16A is a sectional aneurysmic view with a balloon of a third catheter assembly and an associated second extension graft advanced within the first introducer sheath on the ipsilateral side to the septum region of the aortic graft;

FIG. 16B is a sectional aneurysmic view with the first introducer sheath withdrawn to a position downstream of the now exposed second extension graft;

FIG. 16C is a cross-section along line 16C—16C of FIG. 16B; and

DESCRIPTION OF THE PREFERRED EMBODIMENTS

The present invention enables placement of a bifurcated graft at a site of a damaged vessel, such as an artery, by minimally invasive techniques rather than an open surgical access route. Although the methods and apparatus of the present invention are applicable for various types of body lumens, the description herein will be directed to placement of a bifurcated graft within an aneurysm located in the abdominal aorta downstream of the renal arteries for purposes of brevity and simplicity.

In addition, a particular procedure is described herein showing placement of the graft through the right femoral artery of a patient. This method is presently preferred for several reasons. For example, it is contemplated that the bifurcated graft of the present invention will be placed by a vascular surgeon, interventional radiologist or a cardiologist. As a practical matter, physicians are accustomed to placing catheters through a femoral artery entry point, and are less accustomed to other entry points. Further, since most physicians are right handed, the preferred insertion will be in the right femoral artery. By describing this type of insertion, however, it is not intended to exclude other insertion locations, such as the left subclavian artery, or the initiation of the procedure through the left femoral artery. Those of ordinary skill will be able to take the teachings herein and apply them to other body lumens, other lumen locations, and other insertion sites.

As the terms are used herein with reference to the human body, "upstream" pertains to the direction towards the heart while "downstream" pertains to the direction away from the heart. When referring to catheters, "distal" refers to the tip of catheter that is inserted into a patient and "proximal" refers to the end of the catheter outside the body of a patient. The orientation of the graft of the present invention will be referenced with respect to whether it is carried by the catheter or implanted at the aneurysm site. Specifically, upstream and downstream will be used to refer to the portions of the implanted graft closer and farther from the heart, respectively. Alternatively, when the graft is still carried on the catheter, distal and proximal will be used to refer to portions of the graft in accordance with the aforementioned catheter orientation. Finally, ipsilateral refers to the side of the patient in which the primary guidewire and main catheter are inserted (the right femoral artery in the present embodiment), while contralateral refers to the opposite side.

Figure 8A:
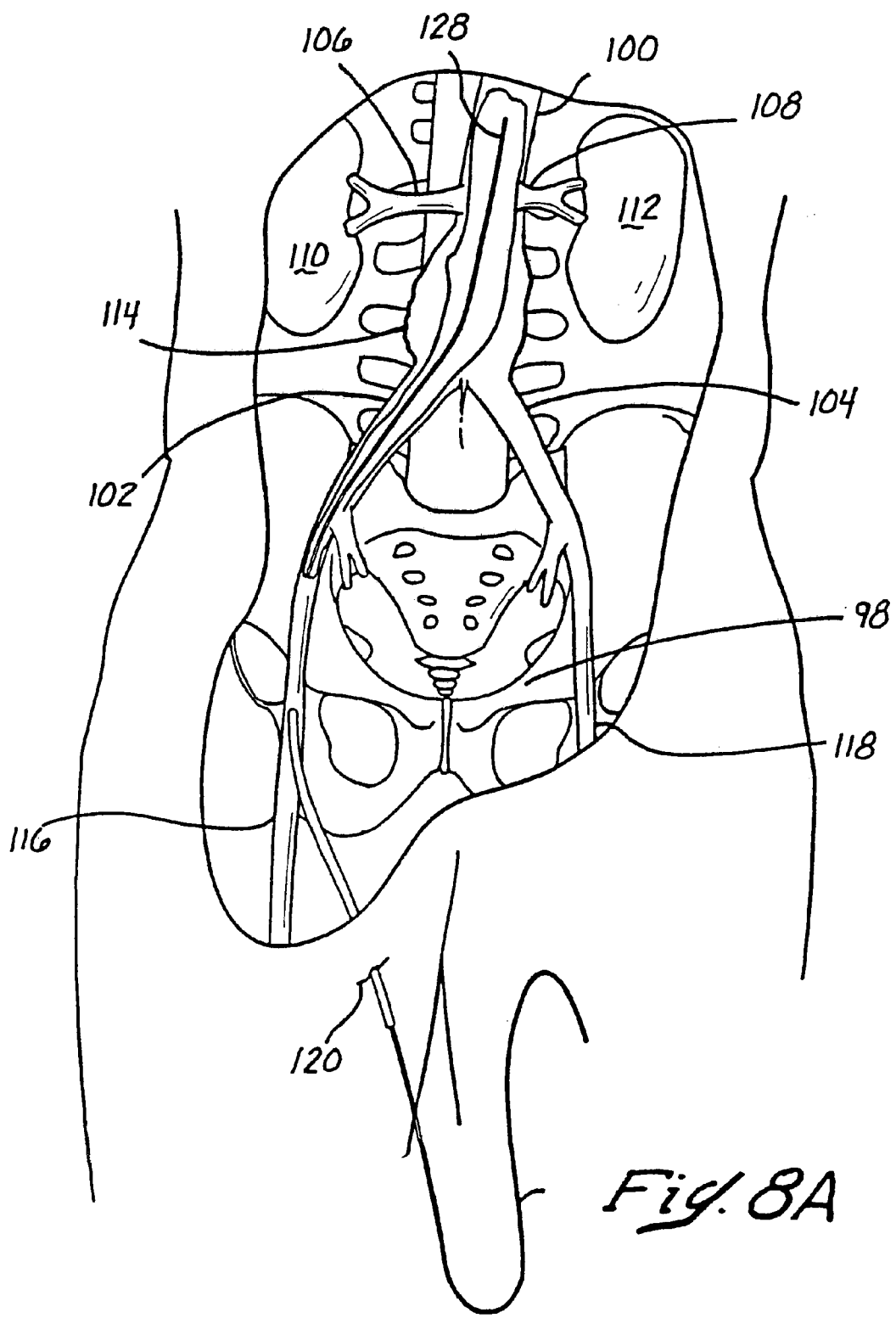
FIG. 8A is a schematic cutaway view of the abdominal region of the human body ("schematic abdominal view") having a guidewire positioned therein.

Aneurysms frequently form in the abdominal aorta at a location between the renal arteries and immediately proximal to the common iliac arteries. FIG. 8A, for example, illustrates the anatomy of the abdomen in the location of an aortic aneurysm. The abdominal aorta 100 can be seen branching distally into the common iliac arteries, the right common iliac artery 102 and the left common iliac artery 104. The right and left renal arteries 106, 100 and the right and left kidneys 110, 112 are located proximal from the common iliacs 102, 104. In between the common iliacs and the renal arteries, an aortic aneurysm 114 can be seen as a bulging section of the abdominal aorta 100. Although not depicted in the present figure, such an aneurysm may even extend down one or both iliac arteries. The right and left common iliac arteries 102, 104 become the right and left femoral arteries 116, 118 in the region of the pelvis 98.

A. Introducer Assembly

It is important to introduce the bifurcated aortic graft of the present invention without causing damage to the patient's vasculature, without undue loss of blood, without dislodging plaque, and with minimum effort. It is a feature of the present invention to utilize an "introducer assembly" to achieve these objectives.

The "introducer assembly" of the present invention is preferably configured for placement over a guidewire. Portions of the introducer assembly are thereafter used to facilitate the advancement of various catheter assemblies required in connection with the practice of the invention as described below. An introducer assembly useful in the practice of the present invention is described in co-pending U.S. patent application Ser. No. 08/713,070 filed on Sep. 12, 1996, incorporated herein by reference (the '070 Application).

The primary components of introducer assembly 130 may be observed by reference to FIG. 3. FIG. 3 depicts a sheath assembly 132. Sheath assembly 132 is comprised generally of a sheath 134 and a valve head 136. Sheath 134 is preferably cylindrical in shape along those portions of its length to be inserted into a patient. Sheath 134 is formed so as to have an appropriate flexibility and an outer diameter suitable for placement at the location of an aneurysm to be repaired. Sheath 134 is provided with a lumen having a diameter suitable to permit insertion of the graft sections and the various catheters described below. Tip portion 138 of sheath 134 is preferably curved so as to minimize any trauma to tissue or tendency to dislodge plaque when the sheath is advanced upstream into a patient's vasculature. As mentioned in the '070 application, tip portion 138 is preferably fitted with a radiopaque marker to assist in proper placement during use.

The femoral artery is a relatively high-pressure lumen. Sheath 134 is fitted with valve head 136 in a fluid-tight fashion. Valve head 136 permits insertion and removal of various catheters during the method of the present invention without significant loss of blood from the femoral artery.

FIG. 3 additionally illustrates a dilator 140 used initially during the insertion of sheath 134 and during, any subsequent upstream movement of sheath 134. Dilator 140 is placed during use through valve head 136 and sheath 134 so that tapered dilator tip portion 142 protrudes from sheath tip portion 138. Dilator tip portion 142 is formed of a somewhat resilient material that is capable of being advanced gently through the tortured pathway of the vasculature without causing undue trauma or a perforation. Yet, it is desired that the tip portion be sufficiently stiff to cause the blood vessels to assume a less tortuous path. In other words, it is intended that the tip portion straighten the vasculature so as to facilitate placement of the sheath. Dilator 140 is provided with a lumen therethrough capable of fitting over a guidewire.

The proximal end of valve head 136 is provided with a threaded connector 144. This threaded connector facilitates fluid-tight connection of the valve head to other catheters during the practice of the method of the invention, as discussed in greater detail below.

The method for insertion of the introducer assembly will now be described. As illustrated in FIGS. 8A and 8B, an incision 120 is made and a primary guidewire 128 is placed in conventional fashion in the right femoral artery 116 and right common iliac artery 102 so as to extend well upstream of the aneurysm 114.

Figure 9B:
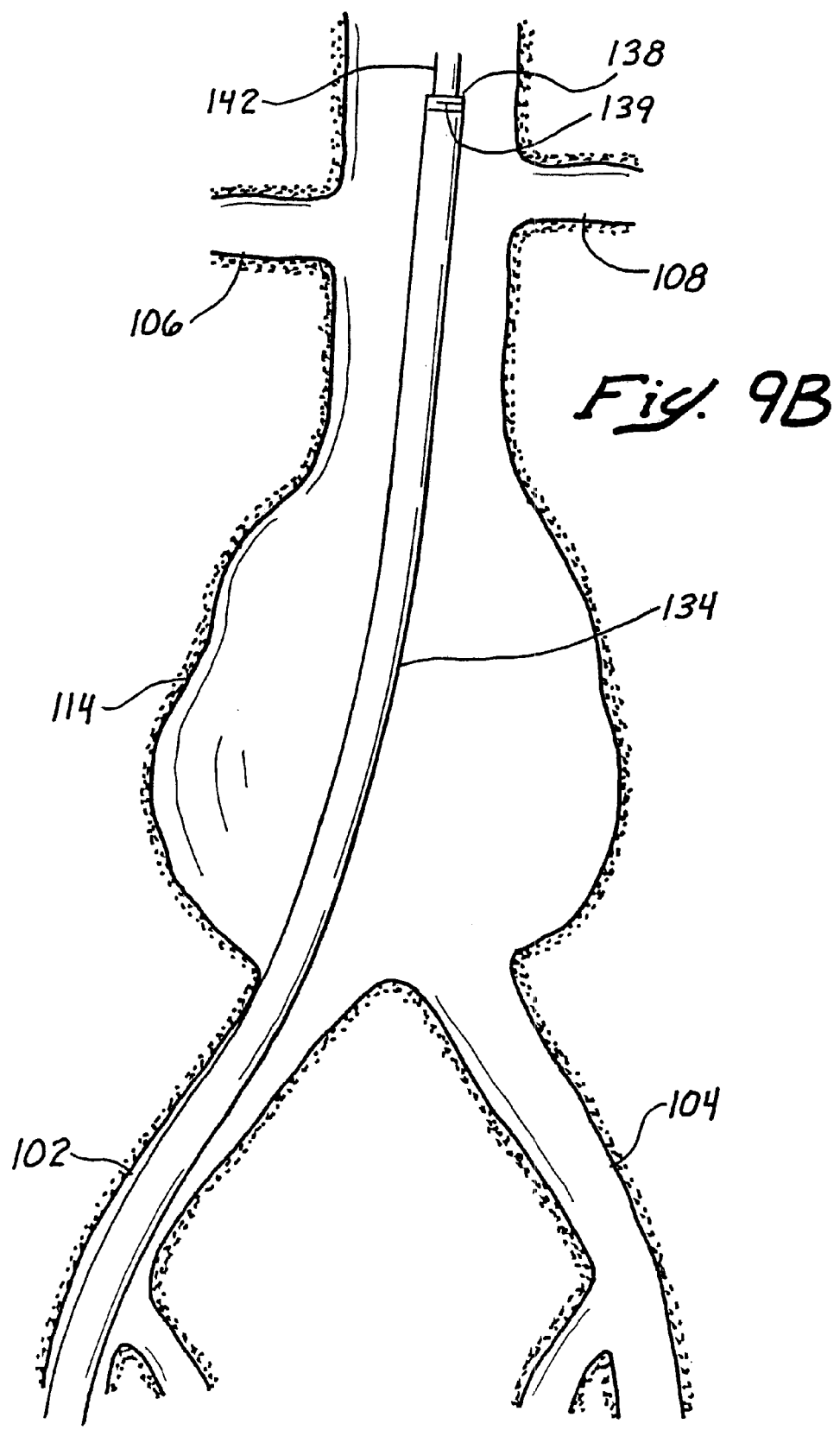
FIG. 9B is a sectional aneurysmic view having an introducer assembly positioned therethrough.

As illustrated in FIGS. 3 and 9A, the introducer assembly 130 (comprising the sheath assembly 132 and the dilator 140) is advanced over and along the primary guidewire 128. As the introducer assembly is advanced, dilator tip portion 142 gently straightens the patient's vasculature in preparation for sheath 134. As seen in FIG. 9B, the introducer assembly is advanced to the point where tip portion 138 of the sheath 134 is upstream from the desired site of graft placement. Specifically, the tip portion 138 is advanced upstream of, one of the two renal arteries 106 and 108 located most proximal to the heart. Under fluorovisualization, a radiopaque marker 139 in sheath tip portion 138 confirms proper placement with respect to the anatomical landmark of the renal arteries.

Figure 9C:
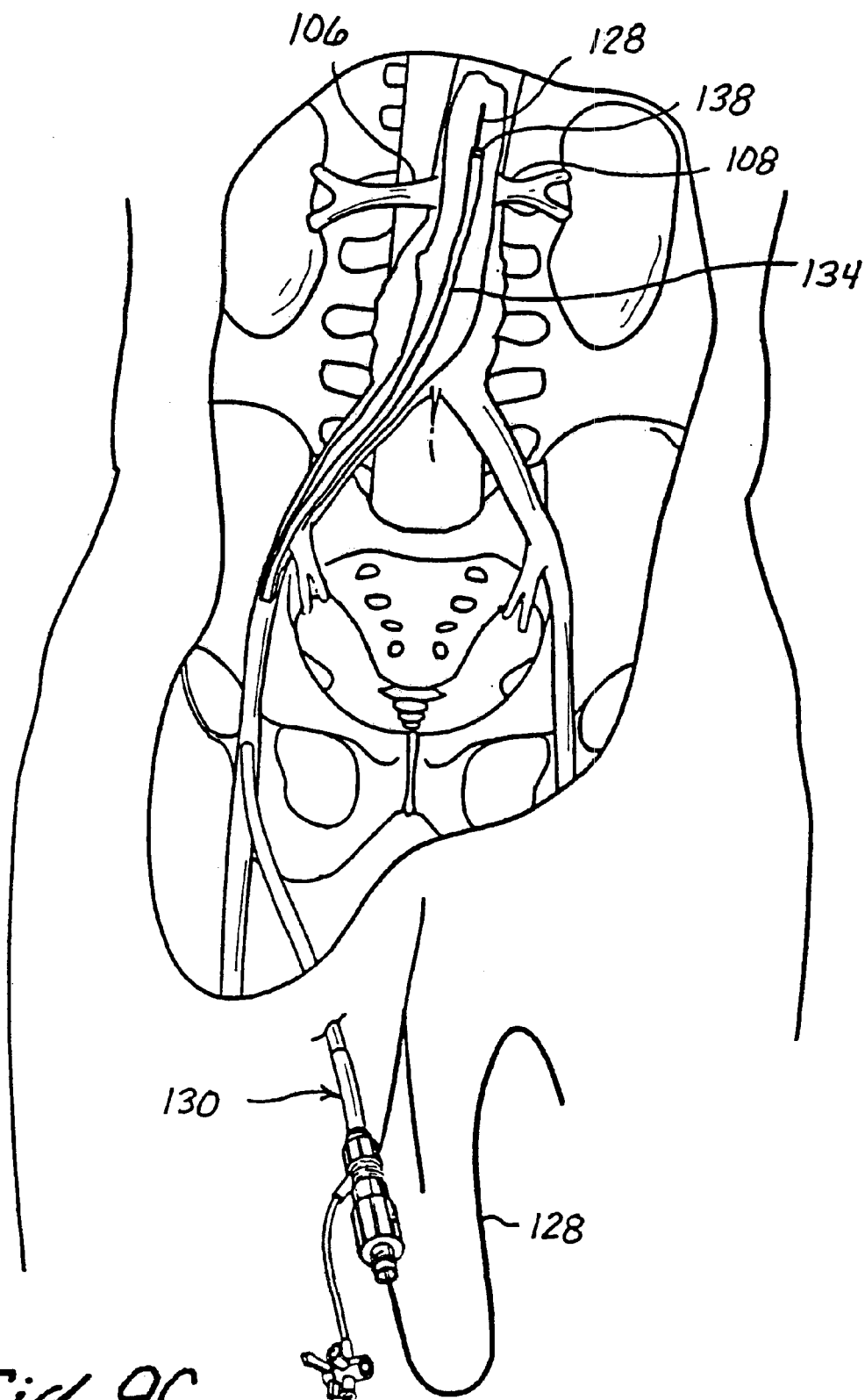
FIG. 9C is a schematic abdominal view with an introducer sheath positioned above the renal arteries and the dilator removed therefrom.

Once the sheath has been properly placed, the dilator 140 (FIG. 3) is retracted along the guidewire and then completely removed from within the sheath assembly 132 and from primary guidewire 128. As illustrated in FIG. 9C, once the dilator 140 has been removed, the lumen of sheath 134 is available for placement of other catheters. Valve head 136 (FIG. 7A) prevents substantial blood loss from sheath assembly 132.

B. Aortic Graft

The aortic graft is designed for introduction into the abdominal aorta with the use of the main loading catheter, which will be described in more detail below. First, the preferred structure of the aortic graft will be described with reference to FIG. 1.

Figure 1:
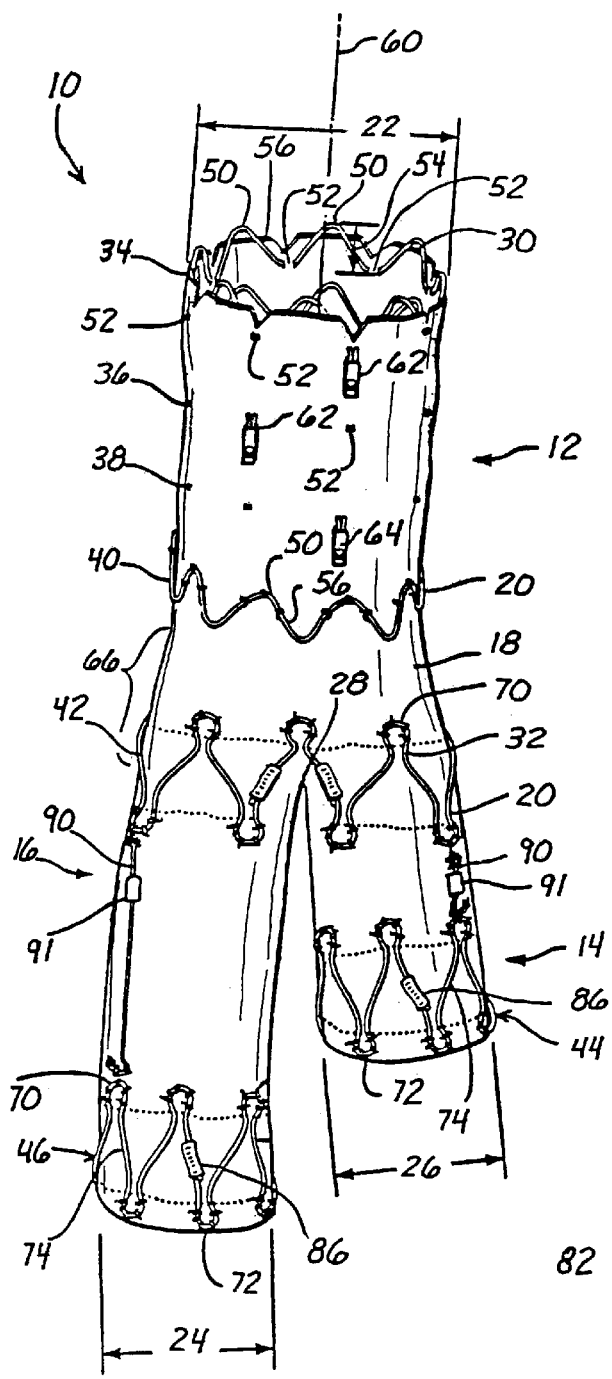
FIG. 1 is a front view of an aortic graft in accordance with the present invention.

As illustrated in FIG. 1, one presently preferred embodiment of the aortic graft is designated generally at 10. Such a bifurcated graft, sometimes referred to as a "trouser graft," is adapted for insertion transfemorally to the situs of an aortic aneurysm in the region where the iliac arteries branch from the abdominal aorta.

The aortic graft 10 includes a proximal trunk portion 12 and is bifurcated to define two proximal legs, a contralateral leg 14 and an ipsilateral leg 16. In this preferred embodiment, the ipsilateral leg 16 extends longer than the contralateral leg 14 to facilitate loading of both legs into a smaller diameter loader when self expanding wireforms are attached to the end of each leg. The length difference between the two legs corresponds to the height of the self-expanding wireform, so that the self-expanding wireforms are not side by side within the loader. This reduces the overall bulk of the graft and permits loading into a smaller diameter loader. One of skill in the art will appreciate, however, that the relative lengths of the two graft legs may be adjusted depending on the particular application for which the graft is to be used. This difference in leg lengths also aids in orientation of the bifurcated graft under fluoroscopy.

The aortic graft 10 is configured from a flexible tubular structure 18 which is reinforced by wireforms 20 extending circumferentially around or woven into the tubular structure 18. The flexible tubular structure 18 is foldable, and the wireforms 20 are radially compressible and expandable. Thus, the graft is configured to move between an insertion diameter, in which state the graft may be inserted intraluminally into the aorta, and a larger, expanded diameter (illustrated in FIG. 1) in which state the graft may be secured within the aorta.

In the expanded state illustrated in FIG. 1, the trunk portion 12 is generally cylindrical and has a trunk diameter 22 corresponding generally to the diameter of an average aorta. In this preferred embodiment, the trunk portion 12 may be configured to be a variety of sizes, one of which is selected according to the size of the abdominal aorta of the patient into which the graft is to be implanted. It is presently preferred to make grafts in which the trunk portion is sized to an expansion diameter of 19, 21, 23, 25, 27, and 29 mm. These sizes, of course, are not limiting of the sizes which may be utilized in accordance with the teachings of the present invention.

As can readily be seen upon inspection of the graft of FIG. 1, the trunk portion 12 defines a cylindrical tube through which fluid may flow. At a septum region 28, the graft bifurcates into the two leg portions 14, 16. The cylindrical tubes defined by the two leg portions are in fluid communication with the trunk portion 12, thereby approximating the internal configuration of the bifurcated junction of the aortic artery. The legs 14, 16 are cylindrical and have diameters which, in their expanded state, correspond to a fixed diameter to insure a constant interface between the legs and the upstream end of the extension grafts which will be described later. In this embodiment, the contralateral leg 14 and the ipsilateral leg 16 have expanded diameters of 13 mm. Again, the magnitude of the expanded diameter of the legs 14, 16 may be varied according to the desired interface between the legs and the extension grafts. However the diameter of the legs is not dependent on the diameter of the trunk region. In prior art bifurcated woven grafts, the leg diameter is one half the diameter of the trunk. For example, a 26 mm trunk would always bifurcate into two 13 mm legs, a 28 mm graft would bifurcate into two 14 mm legs, a 24 mm graft would bifurcate into two 12 mm legs, etc. This is a function of how bifurcated grafts are typically woven.

In the present invention, as shown in FIGS. 2B and 2D, the lower portion of the trunk region can be tapered either out (see FIG. 2B) or in (see FIG. 2D) to insure a constant diameter of the legs regardless of the trunk diameter. For example, as shown in FIG. 2D, a 28 mm trunk would taper down to 26 mm in its lower region prior to being bifurcated into two 13 mm legs. Similarly, as shown in FIG. 2B, a 24 mm trunk would taper out to 26 mm prior to being bifurcated into two 13 mm legs. This provides for a standard leg diameter regardless of the trunk diameter and insures a constant interface and interlock between the bifurcated graft and the extension grafts (see FIGS. 2E through 2G) regardless of the relative diameters of the trunk and the downstream ends of the extension grafts.

An alternative embodiment of this invention would be to maintain a straight trunk through the bifurcation region and then taper the legs either out or in to maintain a constant downstream diameter.

The flexible tubular structure 18 is preferably made of a tube of woven polyester fabric. Although polyester is presently preferred, other materials may be utilized for the flexible tubular structure 18. Such materials include but are not limited to expanded polytetrafluoroethylene (ePTFE), coated polyester, porous polyurethane, silicone, and spun or woven polymeric fibers. One of skill in the art of biocompatible grafts will readily identify other materials suitable for application in the construction of the flexible tubular structure 18. It is preferred that the tubular structure be made of a material which is porous, thereby allowing tissue ingrowth into the graft material and/or formation of an intimal layer, although for some applications it may be desirable to make the tubular structure of a fluid impervious material.

Preferably, the fabric is woven into the tubular configuration, thereby eliminating seams or other internal protrusions which could interfere with blood flow or form locations for thrombi to occur. By employing a flexible fabric for the tubular structure 18, the fabric will readily fold to accommodate radial contraction of the graft, such as is necessary for intraluminal introduction of the graft.

In a preferred embodiment of the present invention, the fabric tubing of the graft and the wireforms therein can be over-sized with respect to the first balloon used to expand the balloon-expandable wireforms. Due to the fact that there is a small amount of recoil that occurs in the balloon-expandable wireforms after expansion, it may be desirable to re-expand these wireforms to more accurately retain the graft within the vessel. If the fabric tubing of the graft and the wireforms have a diameter which is larger than the post-recoil diameter of the wireforms after their first expansion, the physician can use a second, larger balloon to re-expand or over-expand the balloon-expandable wireforms such that upon recoil of the wireforms their diameters are of the proper size for optimum retention of the graft within the vessel.

This feature enables a surgeon to optimize the fit of a graft within a vessel without having to remove it and replace it with another. That is, a graft which upon first balloon-expansion may not sufficiently engage with the wall of the vessel, may be subsequently over-expanded to optimize the fit therein. For example, the fabric tubing of the graft may have a diameter of 24 mm, while the balloon-expandable wireforms have a diameter of 24 mm. The graft is first inflated to 23 mm and the wireforms will recoil to 22 mm. If the physician chooses to further expand the wireforms and more optimally retain the graft in the vessel, the physician will bring in a larger balloon which inflates to 25 mm. After recoil, the final wireform diameter will be 24 mm and the graft will be in its fully opened state.

In accordance with a presently preferred embodiment of the invention, a number of wireforms 20 are provided to furnish structural rigidity to the graft and to secure the graft within the body lumen. As illustrated in FIG. 1, aortic graft 10 includes two different types of wireforms: balloon-expandable wireforms 30 and self-expanding wireforms 32. This preferred embodiment includes three balloon expandable wireforms 34, 36, and 38, which are woven into the fabric but positioned primarily on the interior of the fabric in the trunk region 12 and a single balloon-expandable wireform 40 positioned on the exterior of the fabric at the distal end of the trunk region 12. A self-expanding wireform 42 is attached to the outside of the fabric at the septum region 28 with a self-expanding wireform 44 positioned on the distal end of the contralateral leg 14 and another self-expanding wireform 46 at the distal end of the ipsilateral leg 16.

The balloon-expandable wireforms 30 of the present invention are preferably made of an alloy of carbon, silicon, phosphorus, sulphur, chromium, nickel, beryllium, cobalt, iron, manganese and molybdenum which is sold under the ELGILOY trade name by Elgiloy, L. P. of Elgin, Ill., U.S.A. Other materials which may be utilized in making the wireforms 30 include a nickel and titanium alloy sold under the NITINOL trade name, stainless steel, and other biocompatible, implantable metals. The wires used in manufacturing the balloon-expandable wireforms 30 of the present invention are preferably about 0.012 inches in diameter.

Preferably, each of the balloon-expandable wireforms 30 is similarly configured with a curvilinear geometry such as the closed sinusoidal-like wave geometry illustrated in FIG. 1, with alternating crests 50 and valleys 52 which define an amplitude 54. The amplitude 54 of a wireform is thus defined as the longitudinal distance between a crest 50 and an adjacent valley 52. In this preferred embodiment, the amplitude 54 of the proximal wireform 34 in its expanded state is approximately 0.103 inches.

The balloon-expandable wireforms 30 are preferably configured with a plurality of intermediate segments 56 which are connected by corresponding crests 50 and valleys 52. The crests 50 and valleys 52 are formed with a radius which, in this preferred embodiment, is about 0.025 inches.

Preferably, the intermediate segments are positioned at an angle with respect to each other of greater than about 90 degrees in order to provide greater wireform rigidity, reduced wireform recoil and increased anchoring force. To those ends the intermediate segments are more preferably positioned at an angle with respect to each other from a range of about 100 degrees to about 135 degrees. Most preferably, the intermediate segments are positioned at an angle with respect to each other from a range of about 120 degrees to about 125 degrees.

For example, in the most preferred embodiment, the crests 50 and valleys 52 of the balloon-expandable wireforms 30 are configured by obtaining annealed ELGILOY wire having a diameter of preferably about 0.012 inches and wrapping the wire around a pin having a diameter of 0.050 inches, thereby defining a plurality of adjacent, intermediate segments 56 positioned at an angle with respect to each other of from about 120 to 125 degrees. Thus, the amplitude of the intermediate segments 56 of the proximal wireform 34 in its expanded state (i.e., excluding the radius which defines the crests and valleys) is about 0.103 inches. In this presently preferred embodiment, each balloon-expandable wireform 40 has eight crests 50.

An alternative method for constructing the balloon-expandable wireforms 30 is to configure the wireforms in a true sinusoidal-like pattern. By constructing the wireforms 30 according to this alternative method, the angle between adjacent intermediate portions is about 120 to 125 degrees, thereby maintaining the number of crests on the wireform to eight. Alternatively, the balloon-expandable wireforms are configured such that they are continuously curvilinear as illustrated by FIG. 1B. This continuously curvilinear shape 48 primarily serves to reduce stress on the wireforms when the aortic graft is in its first, compressed state. One of skill in the art will be familiar with other methods for manufacturing balloon-expandable wireforms without departing from the teachings of the present invention.

Because the wire has been annealed, it will readily plastically deform to maintain its configuration. Thus, the wireform may be plastically deformed between the radially collapsed position and the radially expanded position of FIG. 1. The wireforms are, therefore, not resilient to any substantial extent, requiring them to be physically expanded into contact with the internal wall of the aorta via a force other than their own resilience. Further, there is some amount of recoil after balloon-expansion of the wireforms, which will be discussed in more detail below.

The balloon-(expandable wireforms 34, 36, and 38 which are positioned along the proximal portion of the trunk 12 of the graft are preferably secured to the fabric graft material by weaving the wireform through the fabric material. The wire is woven through the fabric such that the distal tip of the valley of each wireform extends through the graft and is positioned on the outside of the fabric structure 18. The weaving is accomplished by initially configuring an elongated piece of wire into the predetermined curvilinear configuration. With the wire so configured, it may be manually woven through the fabric structure 18 until the wire extends around the entire circumference of the fabric structure 18. The wire is woven such that it is primarily positioned along the interior of the fabric tube, with only small segments of wire exposed to the outside of the tube.

The wireform is woven into the fabric tube such that when the wire extends around the entire periphery of the fabric tube, the free ends of the wire protrude from the tube at positions adjacent to each other, thereby enabling a tail segment 62 to be defined by the free ends. The loose ends are preferably held together with a crimping sleeve 64 positioned over them. After crimping the sleeve to secure the ends to each other and thereby complete the ,circular configuration of the wireform, any portion of the wires extending beyond the ends of the sleeve may be trimmed to cleanly finish the tail segment 62. It is preferable that no portion of the wire extend beyond the edge of the crimping sleeve to eliminate the possibility of the wire cutting or piercing the lumen wall.

As illustrated in FIG. 1, the tail segments are positioned on the outside of the fabric layer 18 and extend below the longitudinal position of the other valleys 52 of the wireform. Thus, the most proximal wireform 34 of FIG. 1 includes a tail segment 62 extending in the distal direction below the level of adjacent valleys 52. Although this configuration is preferred, one of skill in the art will appreciate that the wireforms 30 may be formed in two parts with two tails positioned on opposite sides of the graft.

The tail segments 62 of the balloon-expandable wireforms 30 are preferably configured to extend substantially flat against the fabric layer 18, i.e., substantially parallel to the longitudinal axis 60 of the graft. With the tail segments so configured, the risk that the tail segments will penetrate or damage the wall of a lumen with which it comes into contact will be substantially reduced.

The proximal wireform 34 is positioned with respect to the upper edge of the fabric layer such that approximately one-third of the wireform extends beyond the edge of the fabric layer. The wireform is positioned to extend above the edge of the fabric layer to prevent any portion of the fabric layer from oscillating, or "flapping," in response to the flow of blood past the edge of the graft. As an additional measure to prevent such fabric oscillation in the blood stream, the edge of the fabric is configured with V-shaped notches corresponding generally to the valleys 52 of the proximal wireform 34. Thus, the risk of the existence of any loose fabric which could potentially be affected by the passing flow of blood is substantially reduced.

In an alternate embodiment of the present invention, the proximal-most balloon-expandable wireform its preferably configured to have a diameter in its expanded state which is slightly larger than that of the portion of the fabric tubular structure into which it is weaved. Thus, in the illustrated embodiment in which the proximal opening of the fabric portion of the graft has a diameter of 22 mm, the proximal wireform 34 is configured with a diameter of 24 mm. By configuring the wireform to be slightly larger than the fabric into which it is woven, the fabric will be maintained in a constant state of slight tension upon expansion of the wireform, thereby reducing the possibility of the fabric folding or oscillating in response to blood flow through the graft.

Wireforms 36, 38 are positioned adjacent the proximal wireform 34 and are spaced apart from each other such that the wireforms do not interfere with each other in either a radially expanded or contracted state. Thus, for example, in a preferred embodiment the valleys of wireform 34 are located proximal of the crests of wireform 36. The wireforms 34, 36, 38 are also aligned "in phase," with peaks along one longitudinal line and adjacent valleys aligned along a second longitudinal line, thereby further reducing the possibility of overlap of adjacent wireforms. (While there may be some overlapping of the tail segments 62 with an adjacent wireform, because the tail segments extend on the outside of the fabric layer and the adjacent wireform is primarily on the inside of the fabric layer, a small degree of overlap with an adjacent wireform does not pose a problem.)

In addition, adjacent balloon-expandable wireforms are not connected to one another. This coupled with the in-phase configuration of the wireforms maximizes flexibility of the aortic graft without permitting deleterious kinking, which is of primary importance in the often tortuous paths of the abdominal aorta and iliac arteries.

The proximal three wireforms 34, 36, 38 are preferably positioned as close to each other as possible without overlapping. In this embodiment, the wireforms 34, 36, 38 are positioned along the length of the graft about every 4.0 mm. By minimizing the space between the proximal three wireforms 34, 36, 38, the force exerted against the wall of the body lumen is enhanced. Thus, to the extent that the lumen surrounding these three wireforms is healthy and not expanded due to the aneurysm, the wireforms 34, 36, 38 will all assist in achieving a frictional interface with the proximal end of the graft in the lumen.

The distal balloon-expandable wireform 40 is configured similarly to the other balloon-expandable wireforms 34, 36, and 38 in that all are generally circular in cross section.

The distal balloon-expandable wireform 40 is attached to the fabric structure 18 in a different manner from the other balloon-expandable wireforms. Instead of being woven into the fabric structure 18, distal wireform 40 is attached to the fabric by tying it to the fabric with polyester thread. Other biocompatible threads may also be employed for securing the distal wireform 40 to the fabric tubular structure 18. In this preferred embodiment, each crest 50 of distal wireform 40 is secured to the fabric. Each intermediate segment 56 of distal wireform 40 is also preferably tied to the fabric at a point approximately midway between the crest 50 and an adjacent valley 52. Although in this preferred embodiment, wireform 40 is tied to the fabric structure with a thread, one of skill in the art will readily identify other attachment methods. Adhesives, for example, may be successfully employed in accordance with the teachings of the present invention.

Distal wireform 40 is preferably positioned in the transition region 66 to aid in keeping the graft open. In this preferred embodiment, the distal wireform 40 is located approximately 15 mm below the proximally adjacent wireform 38. By positioning the distal wireform 40 in the transition region 66, it will generally be located within the aneurysmic sack when the graft is properly implanted within the lumen of a patient. Consequently, the distal wireform 40 will not engage the wall of the lumen and serves only to provide structural rigidity to maintain the graft open at the transition region 66. Thus, it is preferable that the distal wireform 40 be positioned along the outside of the fabric structure whereas the other balloon-expandable wireforms are primarily located inside of the fabric structure. With the wireform 40 on the outside of the fabric structure, the wireform does not interfere with blood flow through the graft. In addition, it can not be inadvertently snagged from the inside as modular components are introduced into the lumen of the bifurcated graft.

In addition to the balloon-expandable wireforms 30 discussed above, the graft 10 of the present invention also includes a number of self-expanding wireforms 32. The configuration of each of the self-expanding wireforms 32 is naturally biased towards an expanded state, such as that illustrated in FIG. 1. The self-expanding wireforms 32 may be made of the same base material used in the construction of the balloon-expandable wireforms 30, although the method of manufacturing may differ. Thus, ELGILOY wire is preferred, with a number of other materials acceptable for such use.

As illustrated in FIG. 1, the self-expanding wireforms 32 employed in the graft 10 of the present invention have a generally curvilinear configuration having loops which define crests 70 and valleys 72. Further, the intermediate sections 74 are not straight, but have an "S" shape along their length.

Figure 1A:
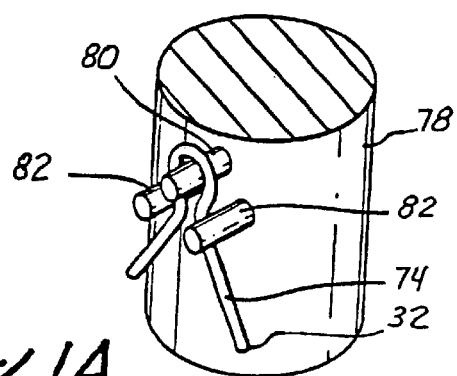
FIG. 1A is a perspective view of a cylindrical mandrel for forming the self-expanding wires of FIG. 1.
Figure 1B:
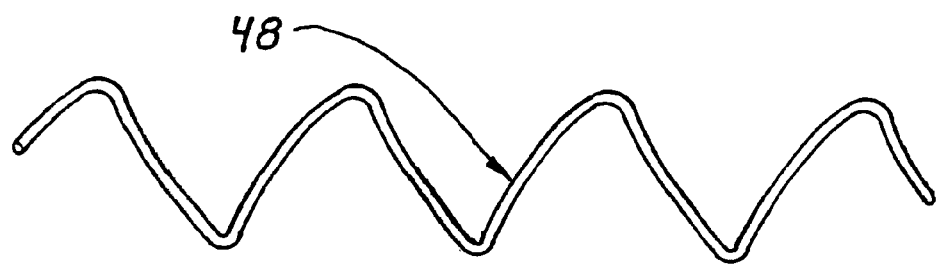
FIG. 1B is a partial plan view of an alternate configuration for a balloon-expandable wireform in accordance with the present invention.

The self-expanding wireforms 32 are constructed by obtaining cold worked ELGILOY wire having a diameter of preferably about 0.012 inches and wrapping it around a cylindrical form 78, such as that illustrated in FIG. 1A, having primary pins 80 positioned to form the loops which define the crests 70 and valleys 72 of the wireform. Two secondary pins 82 are positioned adjacent each primary pin 80 to aid in defining the loops and configuring the "S" shape in the intermediate region 74 of the wireform.

The wireform is thus positioned about the entire circumference of the form 78 and the ends may be fitted with a crimping sleeve while positioned in an overlapping configuration. With the wireform thus configured on the form 78, the wireform and form are placed in an oven heated to about 500 degrees centigrade for about 3.5 to about 5.0 hours. By thus heat treating the self-expanding wireform 32, the wireform will develop a memory corresponding to the shape in which it is positioned on the form. Thus, the wireform may be elastically deformed, such as by radially compressing the wireform for intraluminal insertion into a patient, and, when released, will resiliently return to the shape it had during the heat treatment.

As an alternative method for constructing the self-expanding wireforms 32 of the present invention, a form comprising a flat surface (not illustrated) with a similar pin configuration may be utilized. After heat treating the wireform, the ends of the wireform may be attached, thereby forming the wireform into its cylindrical configuration, according to any of those methods described above.

As the self-expanding wireforms resiliently move between their expanded and contracted positions, tension is applied to the outer portion of the resulting wireform loop and a corresponding compression results on the inner portion of the wireform loop. Thus, the pins 80, 82 of the form 78 are selected to have a radius such that the resulting tension and compression on the loop stay below the yield point of the wire. It has been found that for the preferred embodiment of the self-expanding wireforms 32 illustrated in FIG. 1, a pin diameter of about 0.070 inches is satisfactory and presently preferred.

The self-expanding wireforms 32 are advantageously configured such that the intermediate regions 74 of the wireforms are in an "S" shape. As the wireform moves between its expanded and contracted positions, the elastic deformation which occurs to accommodate such movement is spread substantially evenly throughout the entire length of the wireform. Consequently, the entire length of the wireform acts as a spring to help restore the wireform to its original configuration after radial compression. Thus, the elastic deformation is not concentrated solely in the loops defining the crests and valleys of the wireform, but is also absorbed by the intermediate segments. This reduces the potential for exceeding the yield point of the wire at the crest and valleys of the wireform, which would cause plastic deformation and prevent the wireform from functioning as intended.

With the self-expanding wireforms 32 formed according to one of the methods described above, they may be attached to the fabric tubular structure 18 of the graft 10. Attachment of the self-expanding wireforms 32 is preferably accomplished by tying the crests 70 and valleys 72 to the fabric, as illustrated in FIG. 1. It is presently preferred that each crest and valley be tied in five separate locations around the perimeter of the loop defining the respective crest or valley.

The self-expanding wireforms 32 are designed to have an initial expanded diameter which is slightly larger than the diameter of that portion of the graft where they are to be positioned. It is presently preferred that the wireform be about 2.0 mm larger in diameter than the cross section of fabric to which it is attached. By configuring the wireform with such a relative diameter, the self-expanding wireforms 32, when fully expanded, maintain the fabric structure to which they are attached in a state of slight tension, thereby ensuring that the fabric structure (defining the artificial lumen) is fully open.

Further, the distal self-expandable wireforms exert a radially inward force against the balloon-expandable portions of the graft extensions engaged therewith, as will be described in more detail below with respect to the discussion of placement of the graft extensions.

When designing the wireform, it must also be recognized that the wireform will lose about five percent of its recoil ability after being radially compressed into its state of reduced diameter and subsequently expanded. Thus, for a wireform which is to be positioned at the distal end of either the 13 mm diameter contralateral leg 14 or ipsilateral leg 16, the wireform will initially be designed to have a diameter of about 15.7 mm. After the wireform has been radially compressed and subsequently expanded in a body lumen, it will expand to a diameter of about 14.5 mm—slightly larger than the 13 mm fabric lumen provided at the leg, as desired.

The most proximal self-expanding wireform 42 is positioned at the septum region 28 of the graft. Wireform 42 thus acts to maintain the septum region 28 of the graft open as blood flows through the graft. In this preferred embodiment, the proximal self-expanding wireform 42 is located about 6 to 10 mm distal of the adjacent balloon-expandable wireform 40.

As illustrated in FIG. 1, at the septum region 28 of the aortic graft, the ends of self-expanding septum wireform 42 are secured in crimping sleeves 84, 85. These crimping sleeves are of an outer diameter such that they provide a second function as radiopaque markers. It has been found that for the preferred embodiment of the crimps 84, 85 illustrated in FIG. 1, an outer diameter of at least 0.036 inches is satisfactory and presently preferred. The configuration of these crimping sleeves aids in proper orientation of the aortic graft and confirmation of the location of the septum within the abdominal aorta. The wireform 44 on contralateral leg 14 and wireform 46 on ipsilateral leg 16, similarly include crimping sleeve 86.

Each of the self-expanding wireforms 32 is positioned exteriorly of the fabric tubular structure 18, thereby avoiding interference with blood flow within the graft, and preventing the wireforms from being inadvertently snagged from the inside as modular components are introduced into the lumen of the bifurcated graft. Additionally, the attachment of graft extensions to contralateral leg 14 and ipsilateral leg 16 (explained below) is facilitated by having the wireform positioned on the outside portion of the fabric leg.

The graft 10 is further configured with laterally extending reinforcement wires 90, disposed on each leg 14, 16. The wires 90 are preferably made of the same base material as the wireforms. The wires 90 are positioned on each leg 14, 16 and extend generally from a valley 72 on wireform 42 to a corresponding crest 70 on a respective one of wireforms 44 and 46. As illustrated in FIG. 1, the reinforcement wires 90 are tied onto the fabric structure 18 in a similar manner as are wireforms 32, taking care that the wire 90 does not longitudinally cross into any of the wireforms. The reinforcement wire 90 keeps the legs of the wireform from folding or buckling.

These two longitudinal wireforms 90 are also provided with radiopaque crimps 91 which assist in the placement of the extension grafts within legs 14 and 16.

C. Main Catheter Assembly

The main catheter assembly is utilized to place the aortic graft described above, which is compressed and loaded onto the distal end of the main catheter assembly as will be described in more detail below. A main catheter assembly useful in the practice of the present invention is described in co-pending U.S. patent application Ser. No. 08/713,070 filed on Sep. 12, 1996, previously incorporated herein by reference hereinabove (the '070 Application).

The sheath assembly 132 is utilized to facilitate the operative placement of the main catheter assembly. As such, the main catheter assembly is sized such that it will fit inside the introducer sheath 134.

Figure 6:
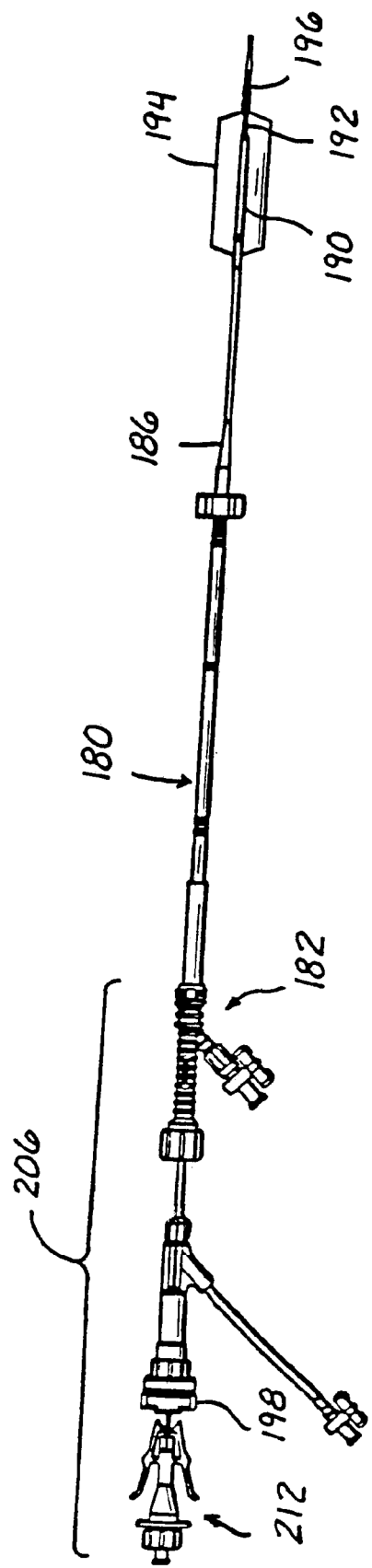
FIG. 6 is a side view of the main catheter assembly of FIG. 4 with the expandable balloon shown exposed arid in an expanded configuration.

The primary components of the main catheter assembly 180 may be observed by reference to FIGS. 4 and 6. The catheter assembly of the present invention comprises a rigid loader 200 which is used to facilitate the operative coupling of the catheter assembly to the introducer assembly during use of the present endovascular delivery system, as will be described in more detail with reference to FIGS. 9B and 9C. The loader comprises an elongate tube 202 including a lumen, a proximal end, and a distal end which is defined by a reduced diameter distal section. An internally threaded connector nut 204 is attached to the distal portion of the elongate tube.

The catheter assembly is cooperatively engaged and secured to the head of the introducer sheath assembly by initially inserting the distal section of the loader into the valve head of the sheath assembly subsequent to the removal of the dilator from therewithin. FIG. 7A. illustrates insertion of the main catheter assembly into the valve head of the sheath assembly. More particularly, the distal section of the loader 200 is extended into the threaded connector 144 of the valve head 136 with the connector nut being threadably engaged to the externally threaded proximal portion of the threaded connector 144. FIG. 7B illustrates the connector nut 204 connected to the valve head 136 of the sheath assembly 132.

The loader and corresponding receiving portion of the valve head are preferably formed of rigid material such that the loader will seat correctly within the interfacing portion of the valve head without flexing or distortion thereof. This ensures proper positioning and registry of the loader and the valve head relative to each other. Furthermore, the ability of the loader to be positively engaged, that is, locked by threadable engagement of the nut to the valve head of the introducer assembly, also facilitates and maintains proper registry and positioning of the loader relative to the introducer assembly.

The catheter assembly of the present invention further includes a proximal connector assembly 206 (FIGS. 4 and 6). The proximal connector assembly includes a pusher connector 182, which is preferably a Y-connector. The proximal connector assembly 206 further includes a tubular body 210 having a lumen extending longitudinally therethrough that is ultimately in fluid communication with the interior of the balloon 194. A tubular side arm 214, which communicates with the lumen of the tubular body, is connected to the tubular body and extends angularly therefrom. A stopcock 218 on the end of the tubular side arm 214 permits valving of the balloon inflation lumen. The proximal connector additionally comprises a Y-connector 208 and a contrast connector 212.

The main catheter assembly 180 further comprises an elongate, tubular pusher body 184. The pusher body 184 includes a distal end 186, a proximal end 188, and a lumen extending longitudinally therethrough. The outer diameter of the distal section slightly exceeds that of the remainder of the pusher body. The proximal end 188 is operatively connected to the pusher connector 182, which along with the pusher body, will expel the loaded aortic graft to leave it in place within the aorta as will be described in more detail below with respect to the preferred method of the present invention.

The main catheter assembly of the present invention further comprises an elongate catheter with a coaxial tube construction. As illustrated in FIG. 6, the elongate coaxial tube catheter comprises an elongate outer tube 190 and an elongate inner tube 192. The outer catheter defines a distal end, a proximal end, and hollow lumen extending longitudinally therethrough. The inner tube is smaller in diameter than the outer tube and extends through the lumen thereof. The inner tube defines a distal end, a proximal end, and hollow lumen extending longitudinally therethrough. The inner tube is slidably extensible distally and retractable proximally relative to the outer tube.

The main catheter assembly further comprises an elongate, inflatable catheter balloon 194, illustrated in its inflated configuration in FIG. 6. This inflatable balloon serves to expand the balloon-expandable reinforcement wires of the aortic graft. When fully inflated, the balloon of the catheter assembly has a generally uniform, cylindrical configuration.

The balloon includes a distal end which is attached to a tubular sleeve portion 196 of the inner tube 192, and a proximal end which is attached to the outer tube 190. In turn, the extension of the inner tube distally relative to the outer tube facilitates the longitudinal stretching of the balloon. The catheter also includes a spacer clip 198 which allows the balloon to be extended or lengthened after deflation thereof to facilitate withdrawal of the balloon and catheter from the expanded aortic graft. The inner tube is initially oriented in a first retracted position relative to the outer tube. The balloon is inflated only when the inner tube is in its retracted orientation.

Subsequent to being deflated, the balloon is preferably stretched longitudinally by the distal advancement of the inner tube of the catheter relative to the outer tube thereof. More particularly, the inner tube is moved from its first, retracted position to its second extended position. The movement of the inner tube from its retracted position to its extended position to stretch the balloon is facilitated by tightly grasping the balloon and contrast connectors of the proximal connector assembly, and subsequently pushing the contrast connector distally toward the balloon connector. Since the outer tube is rigidly attached to the balloon connector and the inner tube is rigidly attached to the contrast connector via the sheath, movement of the contrast connector toward the balloon connector results in a slideable advancement of the inner tube distally within the outer tube. As a result, the attachment of the spacer clip to the exposed portion of the sheath prevents the contrast connector from being moved distally toward the balloon connector. While the spacer clip is in its operative position upon the sheath, the balloon cannot be longitudinally stretched in that the inner tube is prevented from moving from its first, retracted position to its second, extended position. Once the spacer clip is detached from the sheath, the balloon and contrast connectors are no longer maintained in spaced relation to each other so that the contrast connector can be pushed distally toward the balloon connector, thereby facilitating the distal advancement of the inner tube to its extended position and the resultant stretching of the deflated balloon.

The downstream end of the graft ipsilateral leg is trapped between the distal section of the pusher body and the balloon catheter shaft. This facilitates reorientation of the graft during deployment, if desired.

D. Main Graft Deployment

The method for using the main catheter assembly following the withdrawal of the dilator from within the sheath assembly will now be described. Initially, with reference to FIG. 10A, the main catheter assembly 180 is inserted over the primary guidewire 128 and into the sheath assembly 132. The distal connector nut 204 is connected to the threaded sleeve portion of the valve head 136.

Figure 10A:
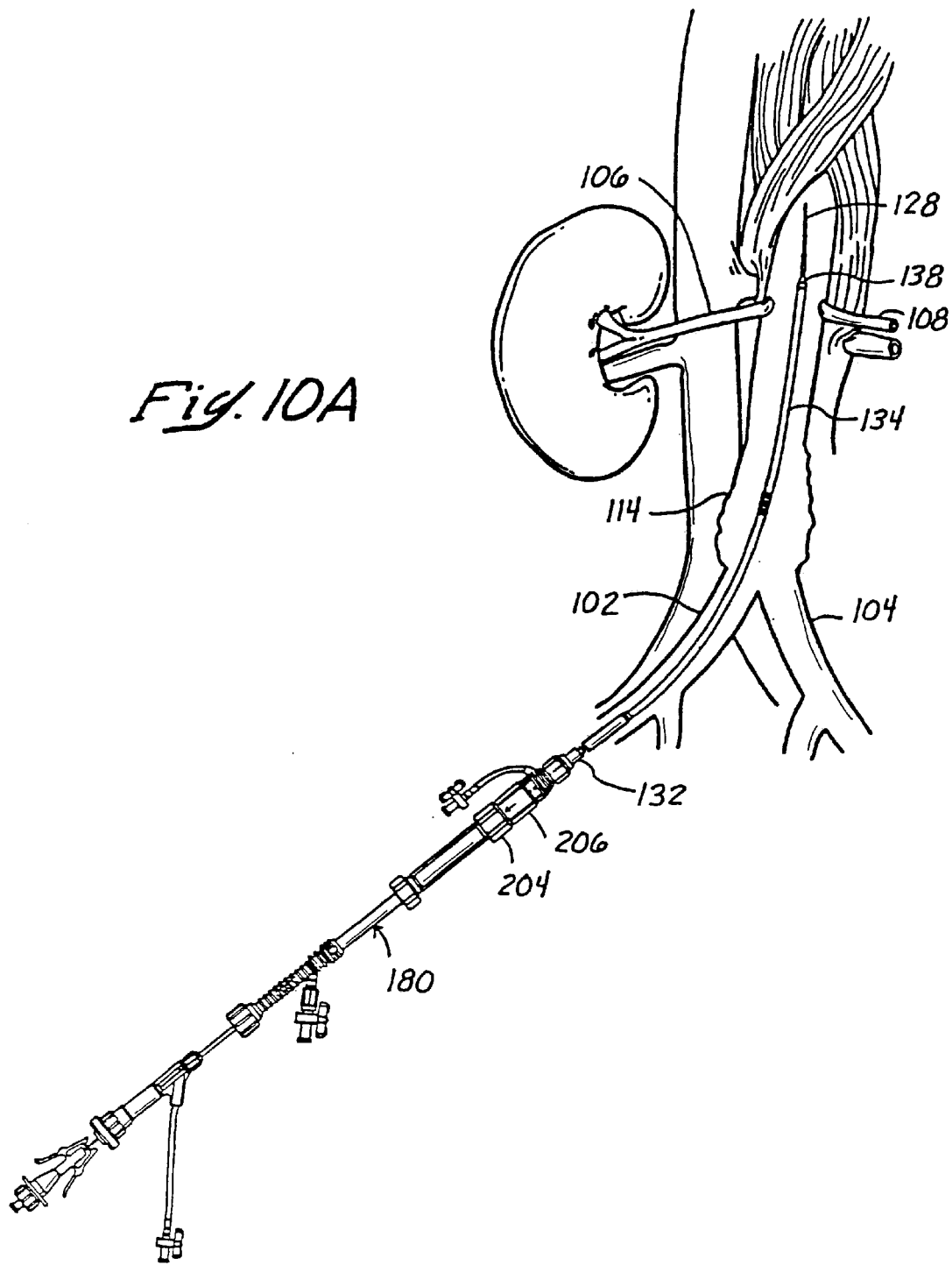
FIG. 10A is, a schematic abdominal view with the balloon of the main catheter assembly and aortic graft advanced within the introducer sheath to the renal arteries.

With reference to FIGS. 10A and 10B, the main catheter is then advanced over the guidewire 128 and within the sheath 134 such that the distal-most portion extends from the sheath tip portion 138, and above the renal arteries 106, 108. To accomplish this, the pusher body 134 (FIG. 4) is distally advanced through the lumen of the introducer sheath 134 until such time as the collapsed graft 10 protrudes from the distal end of the sheath 138. More specifically, as seen in FIG. 10B, the distal end 194a of balloon 194 and the inner catheter 192 protrude from the sheath 134. The precise positioning of the main catheter in this manner is facilitated by observing under fluoroscopy the relative positions of a contrast marker associated with the balloon distal end 194a and the radiopaque marker 139 in sheath tip portion 138. The two radiopaque markers 139, 194a are brought together, with the combination being relatively located with respect to the renal arteries.

The position of the sheath 134 across the aneurysm 114 permits the shielded introduction of the main catheter with balloon 194 and graft 10 thereon into the proper implantation position. In other words, the surrounding sheath 134 shields the advancing catheter and the otherwise expanded and irregularly shaped graft 10 from blood flow resistance. Moreover, the sheath 134 protects the graft assembly from contacting the vessel walls to prevent potential snags. In short, the initial positioning of the sheath upstream of the location at which the graft will be finally implanted ensures that the expanded graft will only have to be displaced downstream into its final location, which is in the direction of blood flow and thus this operation is substantially easier to effectuate and is also less prone to inflict damage on the vessel walls.

Figure 10D:
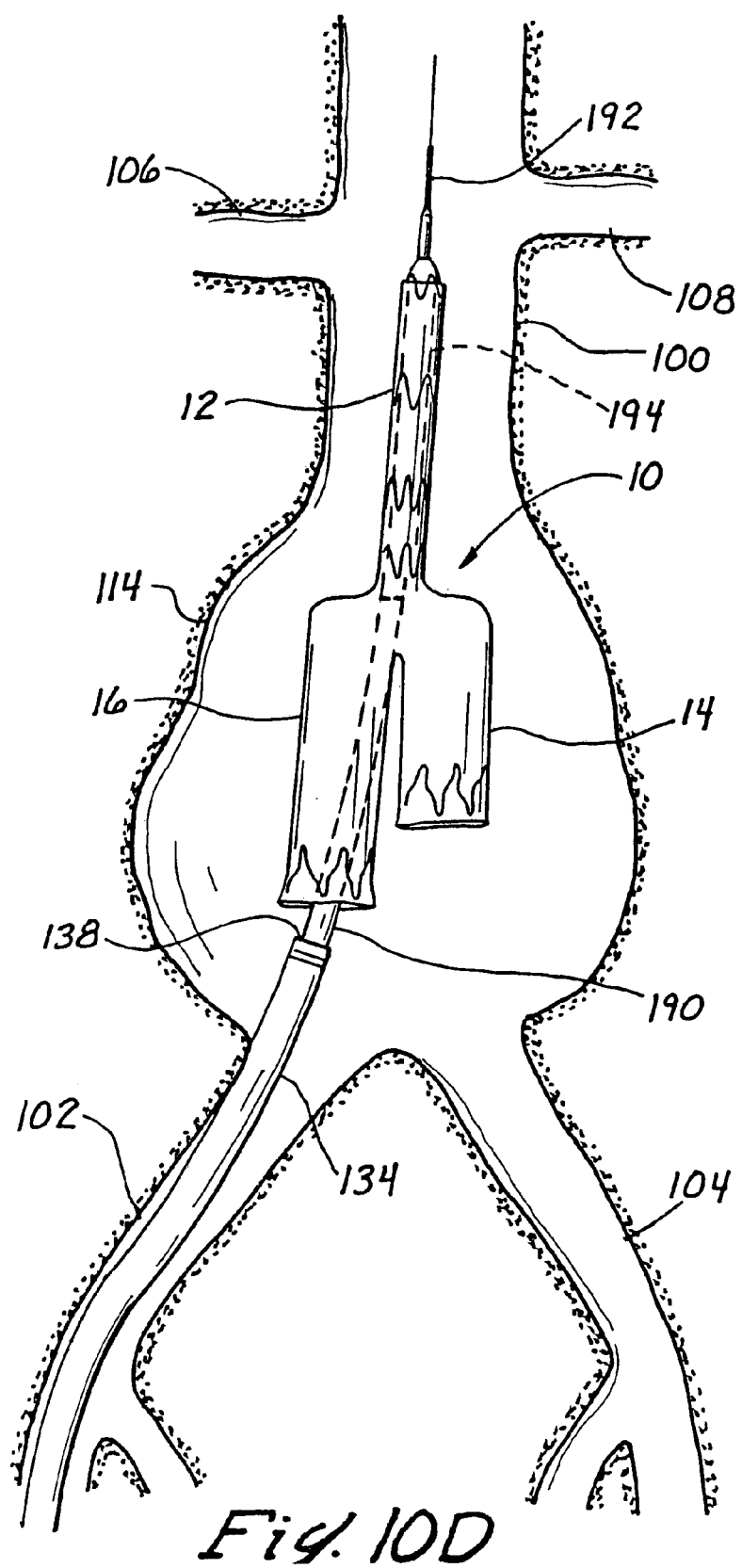
FIG. 10D is a sectional aneurysmic view with the introducer sheath withdrawn to a position downstream of the aortic graft.

Once the graft 10, still within the sheath 134, is positioned upstream from its final location the sheath is removed. FIGS. 10C and 10D illustrate this operation. To accomplish this, the pusher body 184 (FIG. 4) is held stationary as the sheath 134 is withdrawn from the main catheter to a position just downstream from the graft 10. Desirably, as seen in FIG. 10D, the sheath 134 is withdrawn so that the tip portion 138 is just downstream from the longer of the contralateral leg 14 or ipsalateral leg 16. In the case of an enlarged aneurysm 114 as shown, the tip portion 138 will still be within the aneurysm. As the introducer sheath assembly is withdrawn, the self-expanding wireforms 42, 44, & 46 (FIG. 1) in the aortic graft expand within the aneurysm sack, while the balloon-expandable wireforms 30 maintain a substantially compressed configuration.

A final step of positioning of the graft 10 may be required. That is, removal of the sheath 134 from over the graft 10, as seen in FIG. 10C, may leave the distal end of the graft (and distal end of balloon 194a) upstream of the renal arteries 106, 108. (In some instances, removal of the sheath 134 will, by friction, pull the main catheter and graft 10 along with it, though the surgeon is instructed to maintain the catheter position with the pusher body 184. In this respect, the initial positioning of the distal end of the entire assembly upstream of the renal arteries is intended to provide some margin for downstream movement of the catheter). If the contrast marker at the balloon distal end 194a remains upstream of or adjacent to the renal arteries 106, 108, the main catheter is then withdrawn further downstream to reposition the balloon distal end just downstream of the renal arteries. This final position is seen in FIG. 10D. The inflation balloon 194 can be seen in outline inside of the aortic graft 10. The final displacement of the expanded graft 10 downstream is with the blood flow and thus does not require much force.

As seen in FIG. 10D, the graft 10 is sized such that the distal end (as carried on the catheter) thereof protrudes beyond the upstream boundary of the aortic aneurysm and into unaffected region of the abdominal aorta 100. Locating the distal end of the graft 10 just below (downstream from) the renal arteries 106, 108 ensures the maximum length of contact between the eventually expanded graft 10 and the unaffected abdominal aortic wall. The contralateral leg 14 and ipsalateral leg 16 of the graft 10 extend into the aneurysm 114, and, as will be detailed below, extensions thereto are used to continue their respective lumens at least to the unaffected regions of the iliac arteries 102, 104.

Figure 11A:
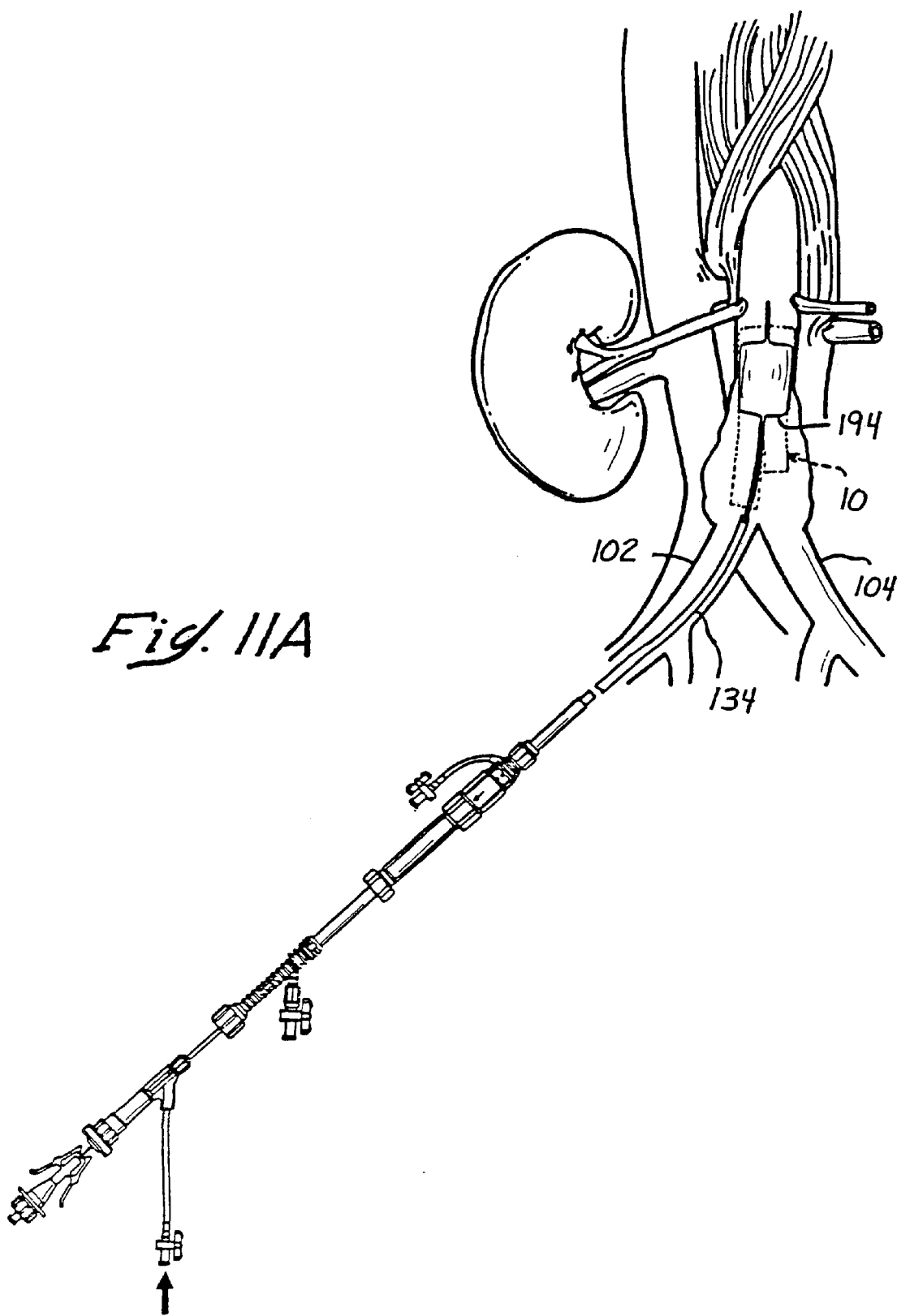
FIG. 11A is a schematic abdominal view with the balloon of the main catheter assembly expanded within a trunk portion of the aortic graft.
Figure 11B:
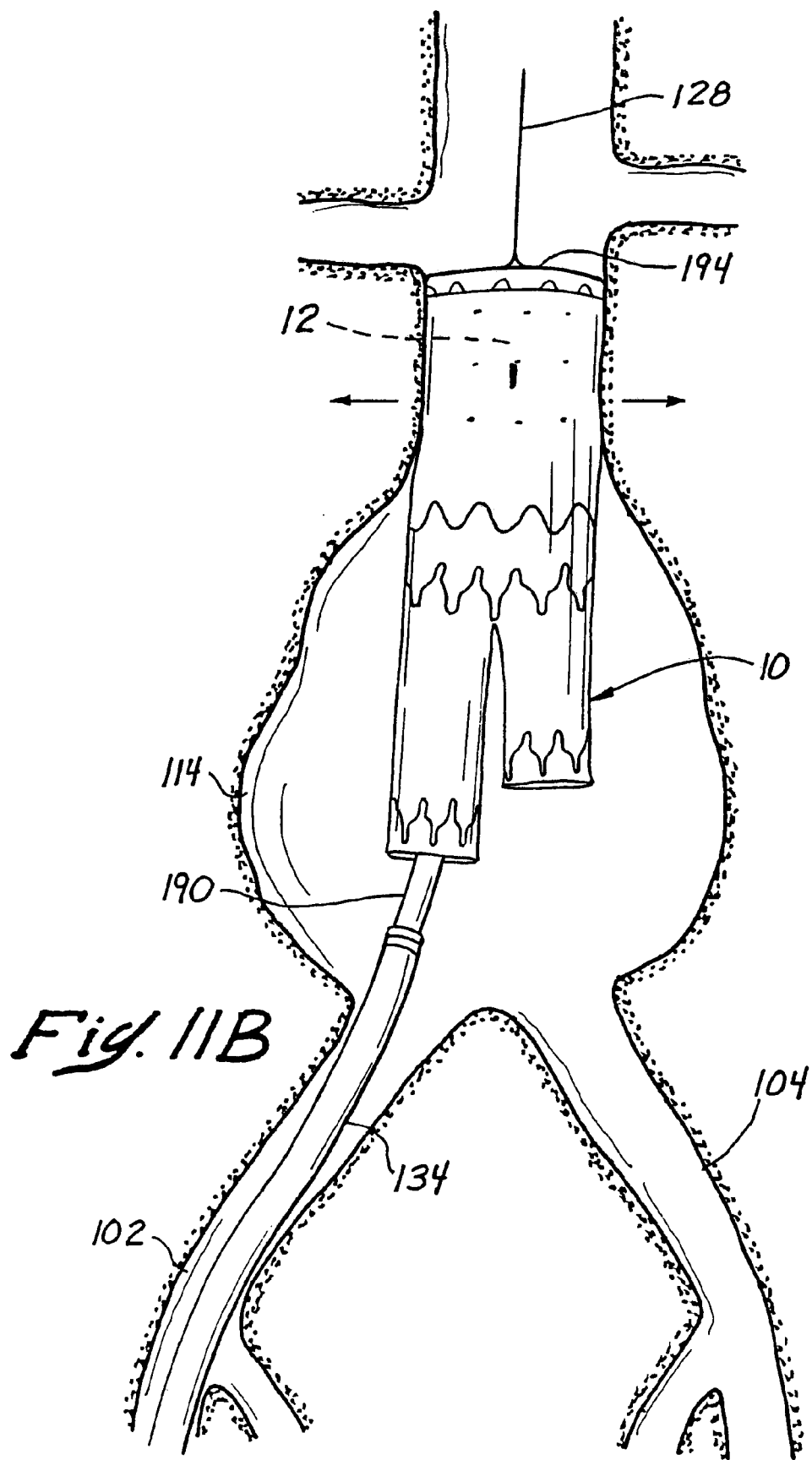
FIG. 11B is a schematic abdominal view with the balloon of the main catheter assembly over-expanded within the aortic graft trunk portion.

As seen in FIGS. 11A and 11B, the balloon 194 is then inflated via the balloon connector. The inflation/pressurization of the balloon causes radial expansion of the trunk portion 12 of the graft 10 from its initial, collapsed orientation, to its second, expanded orientation. Due to the configuration of the balloon when fully inflated, the radial expansion of the trunk portion 12 to its second, expanded orientation is uniform. In this respect, the expansion forces applied to the opposed ends of the trunk portion 12 by the balloon are equal to those applied to the remainder thereof. This uniform application of expansion forces to the trunk portion 12 facilitates the tight engagement of the opposed ends thereof to the luminal surface of the aorta. Preferably, the balloon is inflated for 30 seconds to a pressure of about 2 atmospheres. FIG. 11A, for example, illustrates inflated balloon 194 within the expanded aortic graft 10 (in outline). Further, as illustrated in more detail in FIG. 11B, balloon 194 may be slightly over-sized (represented by the arrows pointing outwardly from the balloon) to force aortic graft 10 into optimal engagement with the aortic wall, especially given the tendency of the wireforms to recoil inwardly slightly after expansion. When the graft is fully expanded, the opposed ends thereof frictionally engage the luminal surfaces of unaffected regions of the aorta.

Figure 12A:
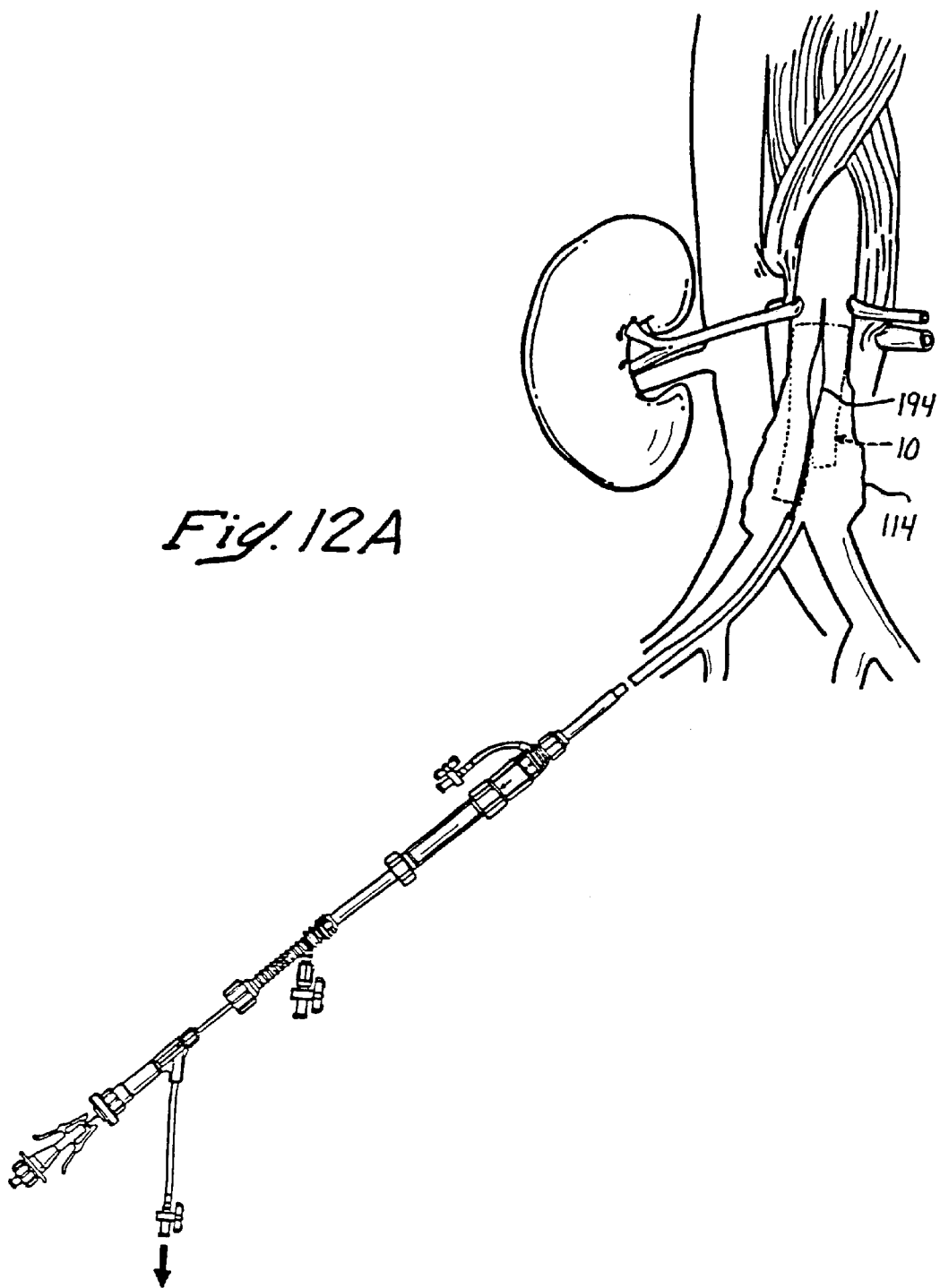
FIG. 12A is a schematic abdominal view with the balloon of the main catheter assembly deflated within the aortic graft.

After the graft has been radially expanded in the aforementioned manner the balloon is deflated and removed from within the sheath 134. As illustrated in FIG. 12A, the balloon 194 is deflated and the stopcock 218 is left open to room air to equalize negative pressure. When the balloon 194 is deflated it may not return to its initial, uninflated orientation due to rigidity of the balloon material. Rather, the diameter of the main body portion of the deflated balloon may remain substantially the same as when the balloon is fully inflated, or may otherwise continue to protrude in a manner that could complicate subsequent retraction and removal of the delivery catheter.

To prevent the deflated balloon 194 from inadvertently catching on or interfering with the radially expanded graft 10 during the withdrawal of the balloon from within, the balloon is longitudinally stretched prior to the withdrawal of the main catheter from within the graft as seen in FIG. 12B. As previously explained, such stretching of the deflated balloon is accomplished by distally advancing the inner tube 192 of the main catheter relative to the outer tube 190 thereof Such movement of the inner tube is facilitated by tightly grasping the balloon and contrast connectors of the proximal connector assembly with the spacer clip removed, and subsequently pushing the contrast connector distally toward the balloon connector, which pushes the distal end of the balloon in the direction indicated by the arrow 216 in FIG. 12B. A vacuum may be pulled through stopcock 218 to completely deflate the balloon 194.

Figure 12C:
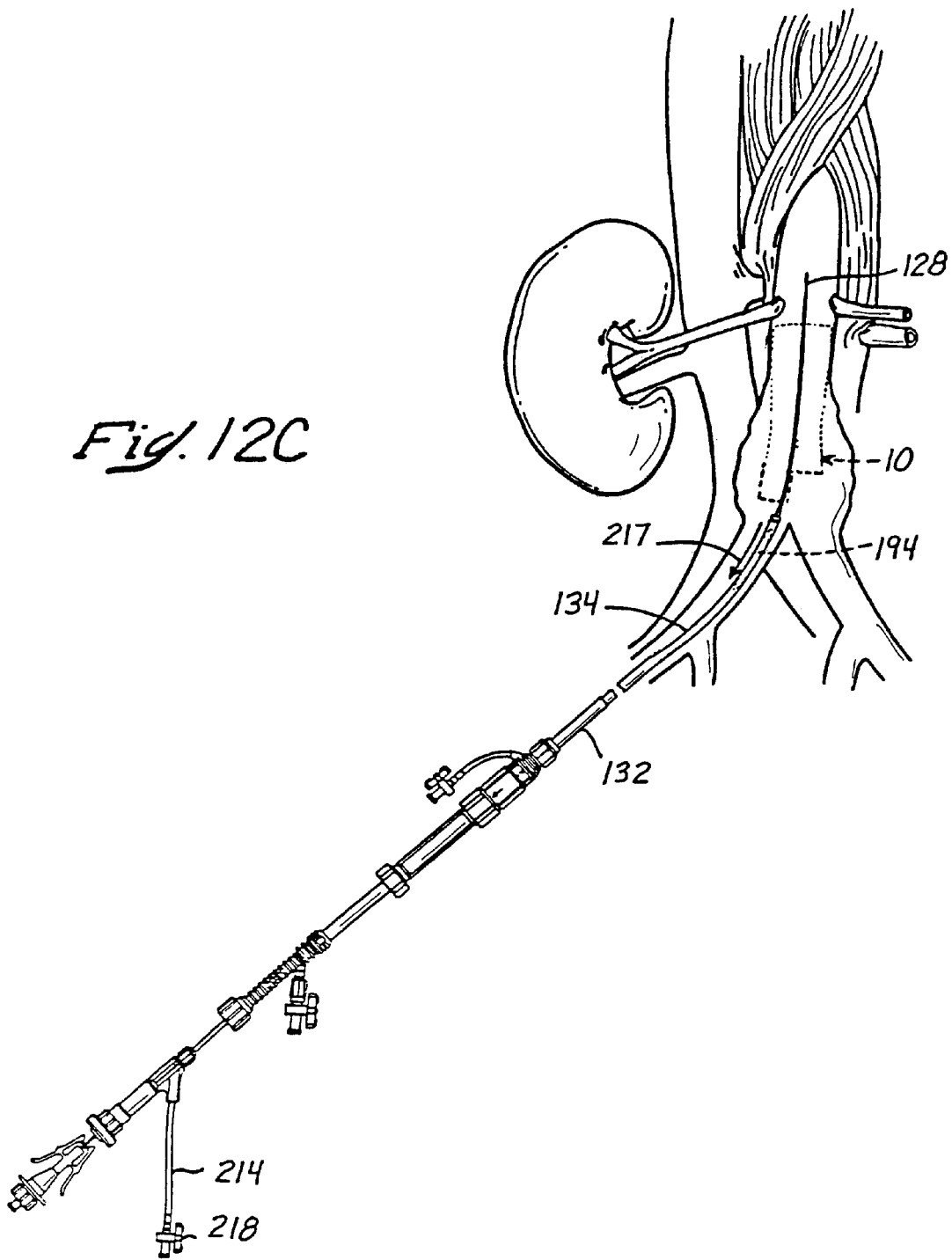
FIG. 12C is a schematic abdominal view with the main catheter assembly being withdrawn therefrom and only the main guidewire extending through the aortic graft.

The main catheter with the now deflated and stretched balloon 194 is then withdrawn slowly and carefully from the aortic graft and into the introducer sheath as illustrated in FIG. 12C. Once the main catheter assembly has been proximally retracted into the introducer sheath 134, it is withdrawn from within the patient's body as indicated by arrow 217. The aortic graft 10 remains in place within the abdominal aorta with the introducer sheath 134 still in position just downstream thereof, and the primary guidewire 128 extending therethrough. It should be noted that the blood flow down the abdominal artery 100 now flows completely through the graft 10; that is, through the trunk 12 and two legs 14 and 16. Attachment of the extensions inside the legs must adapt to this flow, as will be described below.

E. Extension Grafts

As previously described hereinabove, the downstream end of the aortic graft 10 is bifurcated with a septum region 28 separating the ipsilateral leg 16 from the contralateral leg 14. Two additional graft portions are adapted to extend into the respective iliac arteries and to form a frictional engagement with the ipsilateral and contralateral legs of the aortic graft.

These extension grafts typically comprise straight or tapered cylindrical tubes, with an upstream end having a common diameter, while the diameter of the downstream ends can vary depending on the anatomy of the patient (see FIGS. 2E through G). The upstream ends interlock with the respective downstream portions of the aortic graft. By fixing the diameter of the upstream ends of the extension graft and the downstream ends of the bifurcated aortic graft as shown in FIGS. 2B through 2G, a consistent interface and interlock can be achieved regardless of the patients anatomy. The diameter of the downstream end of the graft extensions can be provided in varying diameters so as to suit the diameter of the iliac artery into which graft portions are being implanted. The change in diameter can be provided by a short step-down portion as shown in FIG. 2G, or a step-up portion, as shown in FIG. 2E, or by a region of taper extending along a length of the graft portion.

Figure 2:
FIG. 2 is front view of a graft extension in accordance with the present invention.

Turning now to FIG. 2, one preferred embodiment of a graft extension 170 is depicted. The graft extension comprises an upstream portion 172, a downstream portion 174, and a lumen running the length thereof.

In a preferred embodiment the graft extension 170 is configured from a flexible tubular 175 structure which is reinforced by wireforms 176 extending circumferentially around the tubular structure. The flexible tubular structure is foldable and the wireforms are radially compressible and expandable. Thus, the extension graft is configured to move between an insertion diameter, in which state the graft may be inserted through a femoral and iliac artery and into one of the bifurcated legs of the aortic graft, and a larger, expanded diameter (illustrated in FIG. 2) in which state the graft may be secured within the aortic graft.

In the expanded state illustrated in FIG. 2, the extension graft 170 is generally cylindrical and may be configured to be a variety of sizes, one of which is selected according to the size of the iliac artery of the patient into which the extension graft is to be implanted.

The flexible tubular structure 175 is preferably made of a tube of woven polyester fabric. Although polyester is presently preferred, other materials may be utilized for the flexible tubular structure 175. Such materials include but are not limited to expanded polytetrafluoroethylene (ePTFE), coated polyester, porous polyurethane, silicone, and spun or woven polymeric fibers. One of skill in the art of biocompatible grafts will readily identify other materials suitable for application in the construction of the flexible tubular structure 175. It is preferred that the tubular structure be made of a material which is porous, thereby allowing tissue ingrowth into the graft material and/or formation of an intimal layer, although for some applications it may be desirable to make the tubular structure of a fluid impervious material.

Preferably, the fabric is woven into the tubular configuration, thereby eliminating seams or other internal protrusions which could interfere with blood flow or form locations for thrombi to occur. By employing a flexible fabric for the tubular structure, the fabric will readily fold to accommodate radial contraction of the graft, such as is necessary for intraluminal introduction of the graft.

In one preferred embodiment of the present invention, the diameter of the fabric tubing of the graft is over-sized with respect to the wire-forms therewithin. Upon balloon-expansion of the balloon-expandable wireforms, there is a small amount of recoil that occurs in the wireforms. The fabric tubing of the graft therefore can have a diameter which is larger than the post-recoil diameter of the wireforms. In turn, the wireforms can be over-expanded with a second balloon of a different size such that upon recoil, the diameter of the wireforms is of the proper size for optimum retention of the graft within the vessel. This feature enables a surgeon to optimize the fit of a graft within a vessel without having to remove a too-small graft and replace it with another. That is, a graft which upon first balloon-expansion may not sufficiently engage with wall of vessel, may be subsequently over-expanded by a second balloon of a larger size to optimize the fit therein.

In accordance with a presently preferred embodiment of the invention, a number of balloon-expandable wireforms 176 are provided to furnish structural rigidity to the graft and to secure the graft within the body lumen. Each of the balloon-expandable wireforms is similarly configured with a curvilinear geometry such as the closed sinusoidal-like wave geometry illustrated in FIG. 2A, with alternating crests 150 and valleys 152 which define an amplitude 154. The amplitude 154 of a wireform is thus defined as the longitudinal distance between a crest 150 and an adjacent valley 152.

Alternatively, the balloon-expandable wireforms are configured such that they are continuously curvilinear, such as the configuration of the wireform illustrated by FIG. 1B. As noted above, this continuously curvilinear shape 48 reduces stress on the wireforms when the graft is in its first, compressed state.

An alternative method for constructing the balloon-expandable wireforms is to configure the wireforms in a true sinusoidal pattern. One of skill in the art will be familiar with other methods for manufacturing balloon-expandable wireforms without departing from the teachings of the present invention.

The balloon-expandable wireforms 176 are preferably configured with a plurality of intermediate segments 156 which are connected by corresponding crests 150 and valleys 152. The crests 150 and valleys 152 are formed with a radius which, in this preferred embodiment, is about 0.025 inches.

Preferably, the intermediate segments are positioned at an angle with respect to each other of greater than about 90 degrees in order to provide greater wireform rigidity, reduced wireform recoil, and increased anchoring force. To those ends the intermediate segments are more preferably positioned at an angle with respect to each other from a range of about 100 degrees to about 135 degrees. Most preferably, the intermediate segments are positioned at an angle with respect to each other from a range of about 120 degrees to about 125 degrees.

The balloon-expandable wireforms 176 of the present invention are preferably made of an alloy of carbon, silicon, phosphorus, sulphur, chromium, nickel, beryllium, cobalt, iron, manganese and molybdenum which is sold under the ELGILOY trade name by Elgiloy, L. P. of Elgin, Ill., U.S.A. Other materials which may be utilized in making the wireforms include a nickel -titanium shape memory alloy sold under the NITINOL trade name, stainless steel, and other biocompatible, implantable metals. The wires used in manufacturing the balloon-expandable wireforms of the present invention are preferably about 0.012 inches in diameter.

Because the wire has been annealed, it will readily plastically deform to maintain its configuration. Thus, the wireform may be plastically deformed between the radially collapsed position and the radially expanded position of FIG. 2. The wireforms are, therefore, not resilient to any substantial extent, requiring them to be physically expanded into contact with the internal wall of the iliac artery and downstream legs of the aortic graft via an external force rather than expanding by virtue of their own resilience.

The balloon-expandable wireforms which are positioned along the graft extension are preferably secured to the fabric graft material by weaving the wireform through the fabric material. The wire is weaved through the fabric such that the distal tip of the valley of each wireform extends through the graft and is positioned on the outside of the fabric structure. The weaving is accomplished by initially configuring an elongated piece of wire into the predetermined curvilinear configuration. With the wire so configured, it may be manually woven through the fabric structure until the wire extends around the entire circumference of the fabric structure. The wire is woven such that it is primarily positioned along the interior of the fabric tube, with only small segments of wire exposed to the outside of the tube.

The wireform is woven into the fabric tube such that when the wire extends around the entire periphery of the fabric tube, the free ends of the wire protrude from the tube at positions adjacent to each other, thereby enabling a tail segment 177 to be defined by the free ends. The loose ends are preferably held together with a crimping sleeve 178 positioned over them. After crimping the sleeve to secure the ends to each other and thereby complete the circular configuration of the wireform, any portion of the wires extending beyond the ends of the sleeve may be rimmed to cleanly finish the tail segment.

As illustrated in FIG. 2, the crimping sleeves extend outwardly along the external surface of the extension graft and are radially spaced apart. Preferably, the crimping sleeves on the upstream portion 172 of the extension graft face in a downstream direction, thus frictionally engaging with the wall of the aortic graft body which helps to hold the extension into place. In fact, these upstream crimping sleeves can actually hook on the interior surface of the primary bifurcated graft, thus ensuring no longitudinal movement or separation of the extension graft from the primary aortic graft. The crimping sleeves on the downstream portion 174 face upstream and may frictionally engage, but not penetrate, the wall of the vessel lumen within which the device is placed. The crimping sleeves act as radiopaque markers, particularly for aiding in the placement and positioning of the graft extensions.

The most proximal wireform 168 and the most distal wireform 166 are positioned with respect to the upper and lower edge of the fabric layer such that approximately one-third of the wireform extends beyond the respective edge of the fabric layer. In particular, the proximal-most wireform is positioned to extend above the edge of the fabric layer to prevent any portion of the fabric layer from oscillating, or "flapping," in response to the flow of blood past the edge of the graft. As an additional measure to prevent such fabric oscillation in the blood stream, the proximal and distal edges of the fabric are configured with V-shaped notches corresponding generally to the valleys 152 of the proximal and distal wireforms. Thus, the risk of the existence of any loose fabric which could potentially be affected by the passing flow of blood is substantially reduced.

In an alternate embodiment of the present invention, the proximal-most balloon-expandable wireform is preferably configured to have a diameter in its expanded state which is slightly larger than that of the portion of the fabric tubular structure into which it is weaved. By configuring the wireform to be slightly larger than the fabric into which it is woven, the fabric will be maintained in a constant state of slight tension upon expansion of the wireform, thereby reducing the possibility of the fabric folding or oscillating in response to blood flow through the graft.

Additionally, the proximal balloon-expandable wireforms on the graft extension work in concert with the distal self-expandable wireforms on the aortic graft to hold the graft extensions in place. The balloon-expandable wires can be expanded slightly beyond the diameter of the distal self-expandable wireforms. This will cause the distal self-expandable wireforms to exert a radially inward pressure against the balloon-expandable portions of the graft extensions, thereby enhancing the frictional interface between them and providing a tighter seal.

In a preferred embodiment of the present invention, the wireforms are positioned adjacent one another and are spaced apart from each other such that the wireforms do not interfere with each other in either a radially expanded or contracted state. Thus, for example, the valleys of one wireform are located proximal of the crests of the next adjacent wireform. Preferably, the wireforms are also aligned "in phase," with peaks along one longitudinal line and adjacent valleys aligned along a second longitudinal line, thereby further reducing, the possibility of overlap of adjacent wireforms. (While there may be some overlapping of the tail segments with an adjacent wireform, because the tail segments extend on the outside of the fabric layer and the adjacent wireform is primarily on the inside of the fabric layer, a small degree of overlap with an adjacent wireform does not pose a problem.)

In addition, adjacent balloon-expandable wireforms are not connected to one another. This coupled with the in-phase configuration of the wireforms maximizes flexibility of the aortic graft without permitting deleterious kinking, which is of primary importance in the often tortuous paths of the abdominal aorta and iliac arteries.

An important feature of the extension grafts of the present invention is the spacing distance between adjacent wireforms. It has been discovered in accordance with the investigations of the present invention that optimizing the spacing distance between the wireforms improves the balance between kink resistance and flexibility in the graft extensions. Too much space promotes kinking, while too little space detracts from flexibility. These are important features in the often tortuous path of the iliac arteries and abdominal aorta in which the graft extensions are to be placed.

Figure 2A:
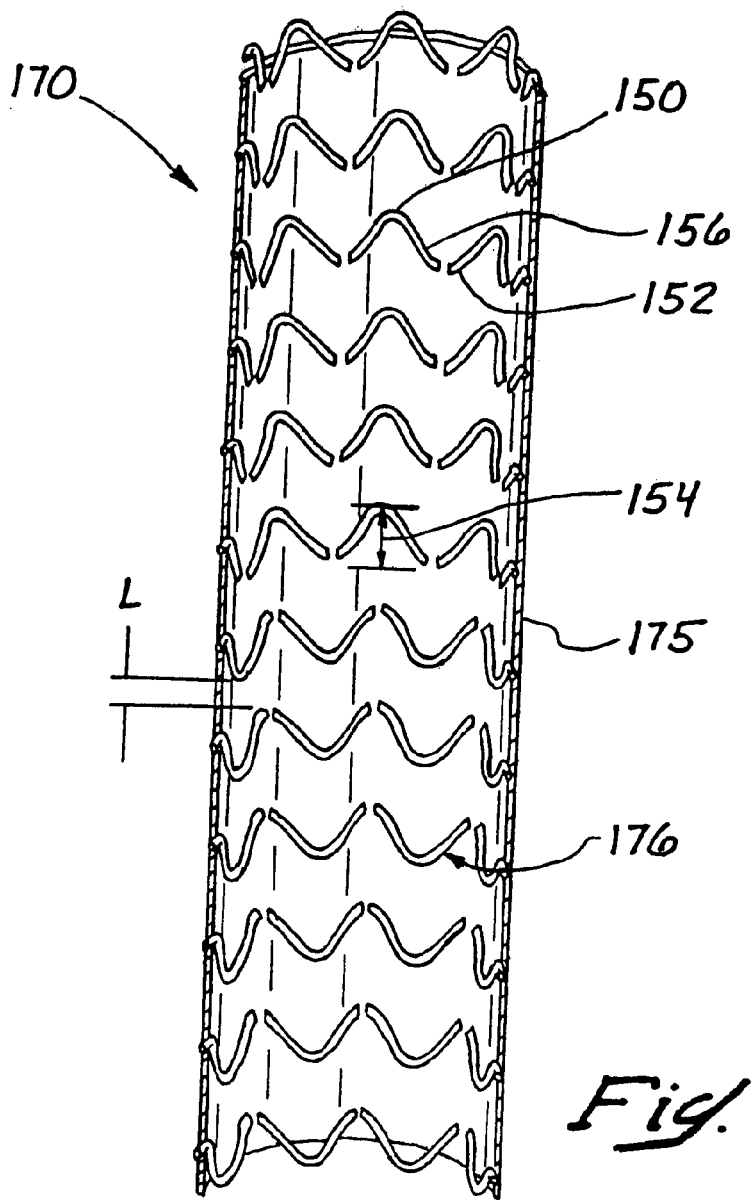
FIG. 2A is an internal cross-sectional view of the graft extension from FIG. 2.

FIG. 2A, for example, illustrates in cross-section balloon-expandable wireforms 176. Preferably the length "L" or separation distance between adjacent wireforms is measured from the closest point on each neighboring wire. For example, in FIG. 2A, L is the distance between crest 150 and valley 152.

Further, the graft extensions have a diameter "D" which varies according to the differently sized extensions. In one embodiment the length L between adjacent wireforms is preferably less than 2D. In a preferred embodiment the length L between adjacent wireforms will be less than D. In another preferred embodiment the length between adjacent wireforms will be less than D and greater than zero. Therefore, the preferred separation distance depends on the diameter of the graft.

In a 14 mm graft a preferred separation distance between adjacent wireforms that has been found to be acceptable during use is 2.4 to 2.5 mm.

Further, as discussed above, the interface between the upstream portion of the extension graft and the downstream leg of the aortic graft is preferably standardized such that the downstream legs and the upstream extensions have the same dimension at their interface, regardless of the diameter of the aorta above the aneurysm and the diameters of the iliac arteries below the aneurysm.

F. Directional Catheter

The present invention further includes a directional catheter. The structure of this catheter is substantially disclosed in WO 97/26936, which was previously incorporated by reference hereinabove. Specifically, the directional catheter facilitates guidewire access to the contralateral leg of the bifurcated graft to allow placement of a contralateral extension graft into the bifurcated graft.

Figure 5:
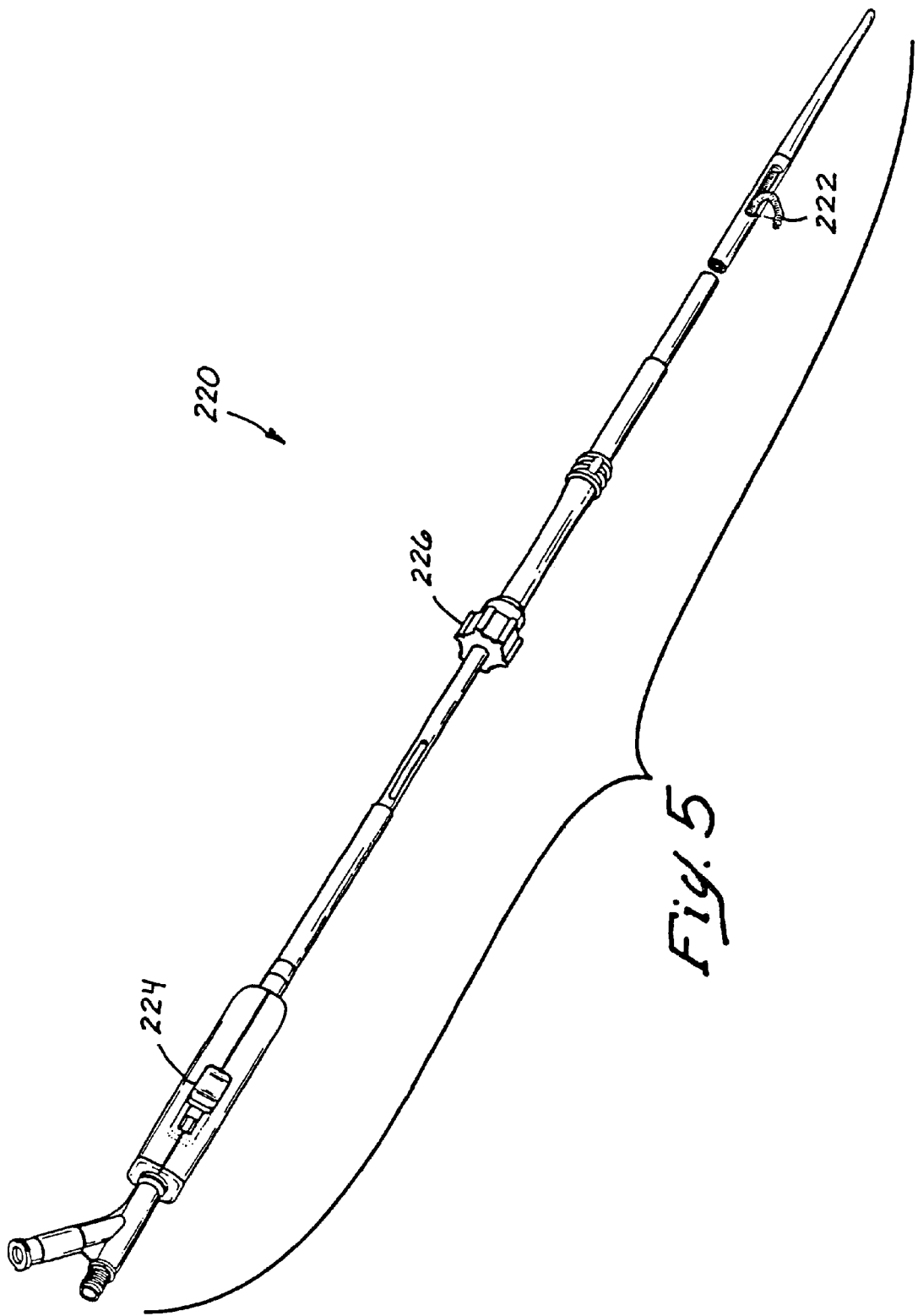
FIG. 5 is a front perspective view of a directional catheter assembly of the present invention.

The primary components of directional catheter 220 may be observed by reference to FIG. 5. The directional catheter includes a deflecting spring portion 222, (illustrated substantially deflected). Knob 224 is used to deflect the spring portion. Connector nut 226 is provided such that the directional catheter can be operatively connected with the sheath assembly.

G. Extension Graft Deployment

Figures 13A, 13B:
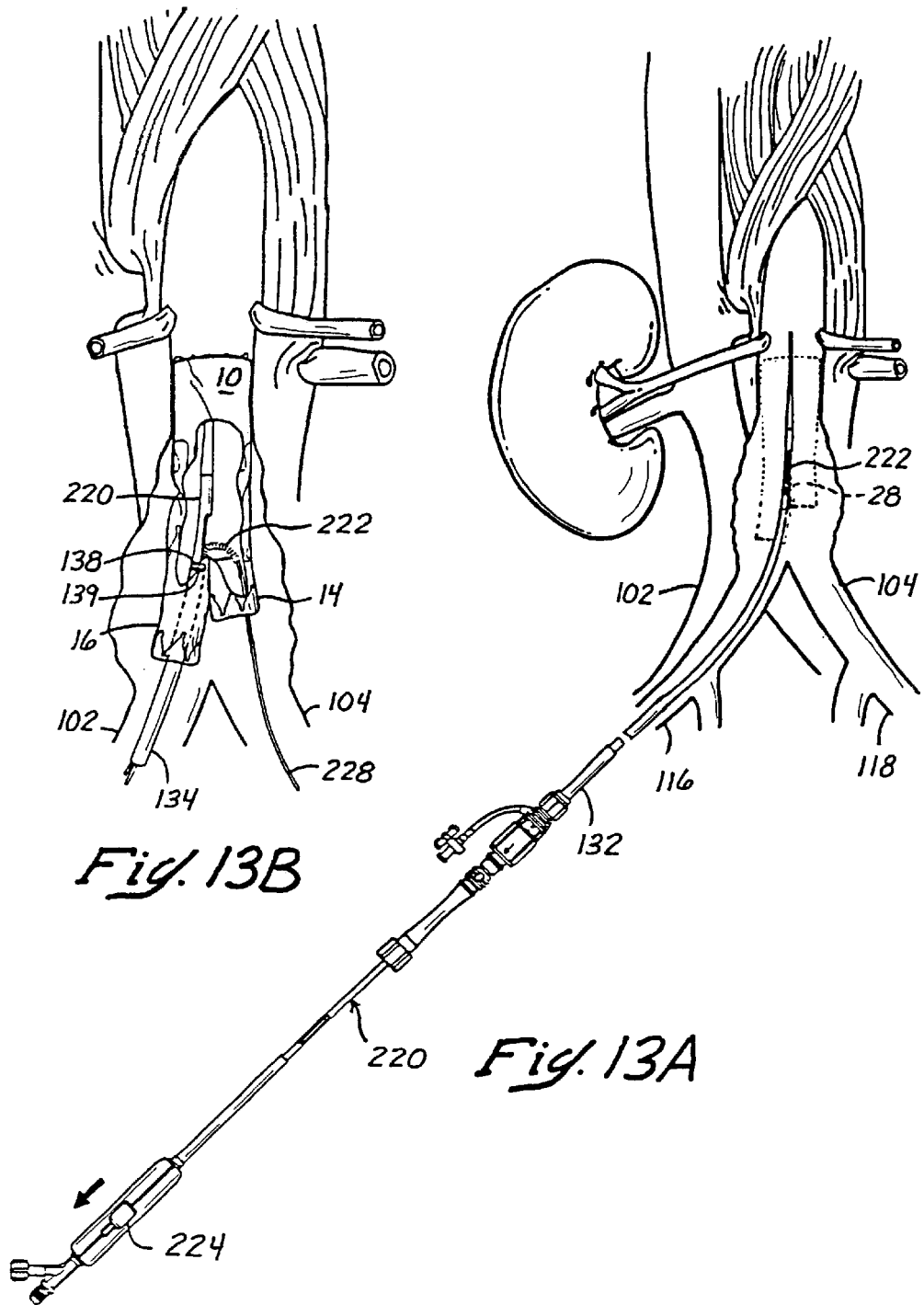
FIG. 13A is a schematic abdominal view with the directional catheter connected to the sheath assembly and positioned within the aortic graft.
FIG. 13B is a detailed view of the directional catheter being deflected around the septum region of the aortic graft.

The procedure for attaching the extension tubes will now be described. With reference to FIGS. 13A and 13B, the sheath 134 stiffened by a dilator (not shown) is advanced over the guidewire 128 until the distal tip 138 is located approximately at the septum region 28. The location of the distal tip 138 is again facilitated by fluoro-visualization of the marker 139 with respect to the radiopaque crimping sleeves 84, 85 (FIG. 1) on the graft 10. The dilator is then proximally withdrawn from within the sheath 134, and the directional catheter 220 advanced distally over the guidewire 128 and within the sheath 134 to project a short distance from the distal tip 138 (FIG. 13B).

More particularly, the directional catheter 220 is first inserted over the primary guidewire through the ipsilateral side, for example, through the right femoral artery 116 and the right common iliac artery 102 in the present case. FIG. 13A illustrates the directional catheter 220 operatively connected to the sheath assembly 132. The spring portion 222 of the directional catheter 220 is positioned such that it is above the septal region 28 of the aortic graft 10. Proper positioning of the spring portion to the contralateral side is adjusted by rotating or advancing forwards or backwards the whole directional catheter 220 while under fluoro-visualization. The spring portion 222 is deflected by pulling knob 224 in the direction of the arrow in FIG. 13A. FIG. 13B illustrates the deflected spring portion 222 positioned within the contralateral leg 14.

A supplemental guidewire 228 is then advanced through the directional catheter 220 and out the deflected spring portion 222 to extend down the contralateral leg 14 and through the left common iliac artery 104. The supplemental guidewire 228 is extended until it is in the left femoral artery 118, at which time the left femoral artery is cross-clamped and a cut-down or percutaneous incision is performed to retrieve the supplemental guidewire. If the guidewire has not been guided fully along the femoral artery a snare or similar device can be introduced through the left femoral artery to grab the guidewire and draw it back to the puncture or incision site for retrieval.

Figure 13C:
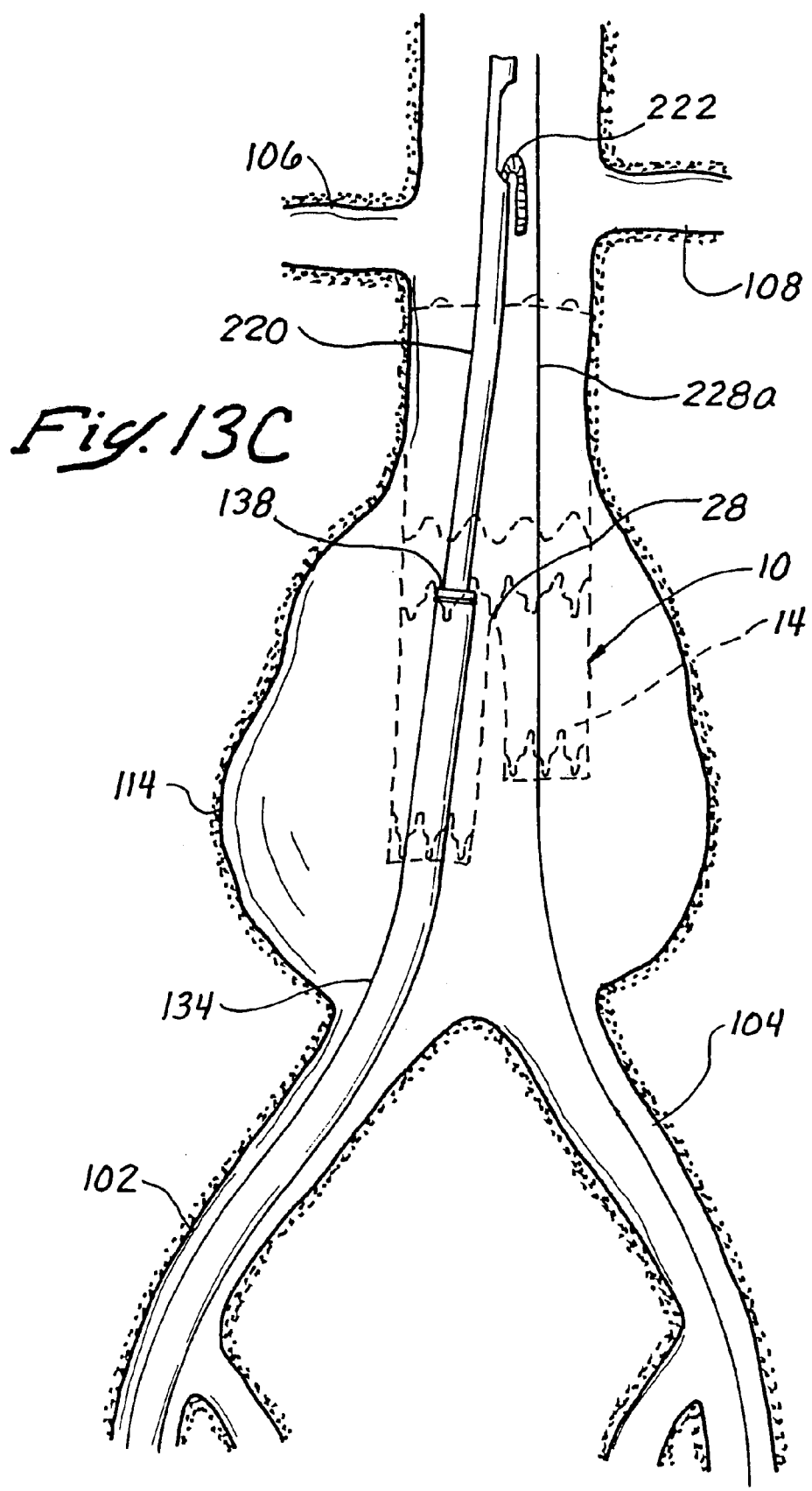
FIG. 13C is a sectional aneurysmic view with the directional catheter advanced to a position above the renal arteries and a second guidewire positioned within the contralateral side.

As seen in FIG. 13C, once the supplemental guidewire 228 is in place through the left common iliac artery 104 the directional catheter 220 is advanced distally through the bifurcated graft 10 and into a position above the renal arteries 106, 108. The spring portion 222 remains deflected to present a curvilinear upstream profile. This curved profile enables advancement of the directional catheter 220 without risk of the distal end of the spring portion 222 snagging on the openings to the renal arteries 106, 168. The directional catheter 220 remains in this position while the tubular graft extension 170 is attached to the contralateral leg 14. A stiffer guidewire 228a is then exchanged with the supplemental guidewire 228 by conventional methods to extend through the left iliac artery 104 and within the contralateral leg 14 of the aortic graft.

Figure 14A:
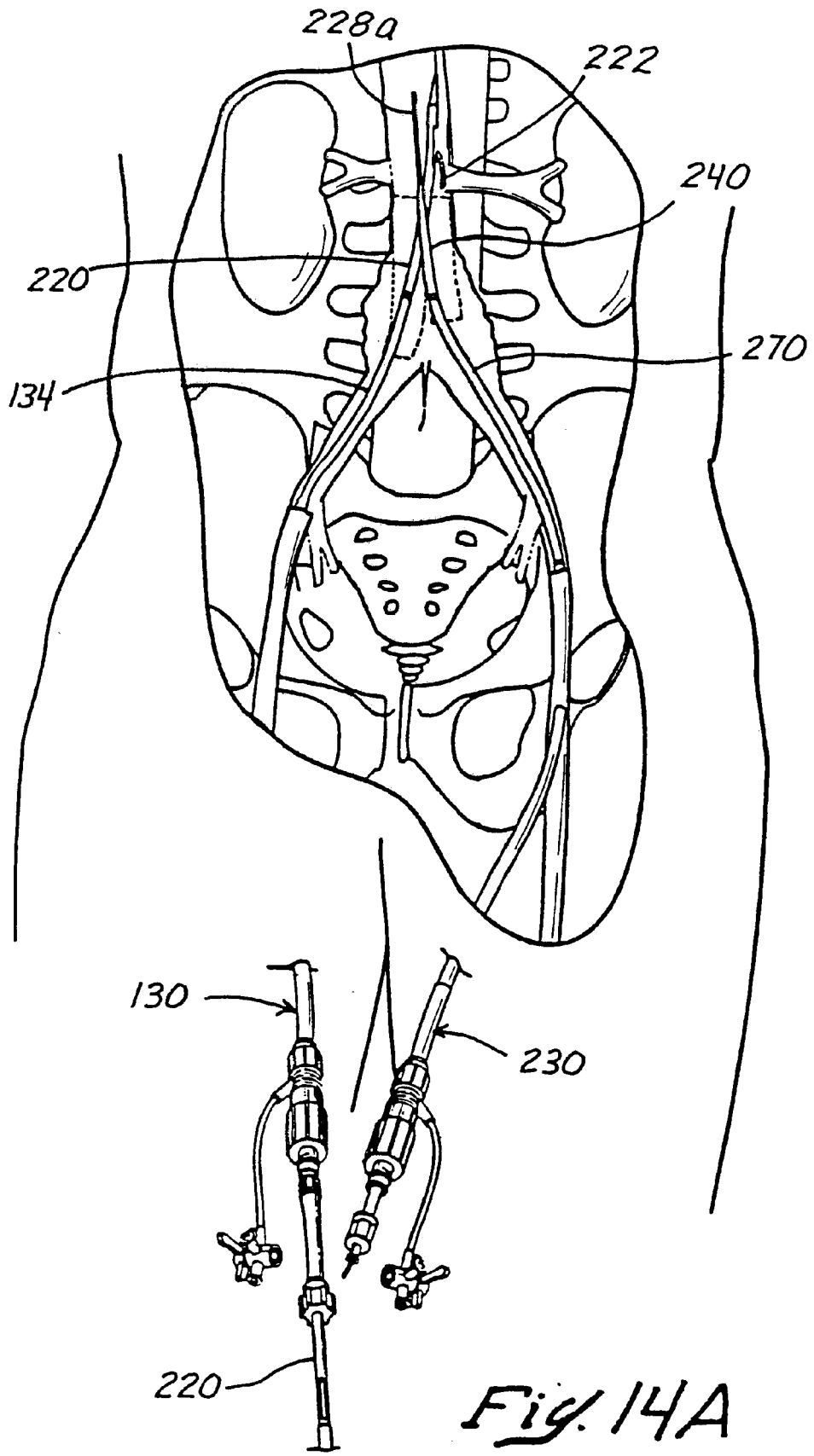
FIG. 14A is a schematic abdominal view with a second catheter assembly positioned within the contralateral side.
Figure 14B:
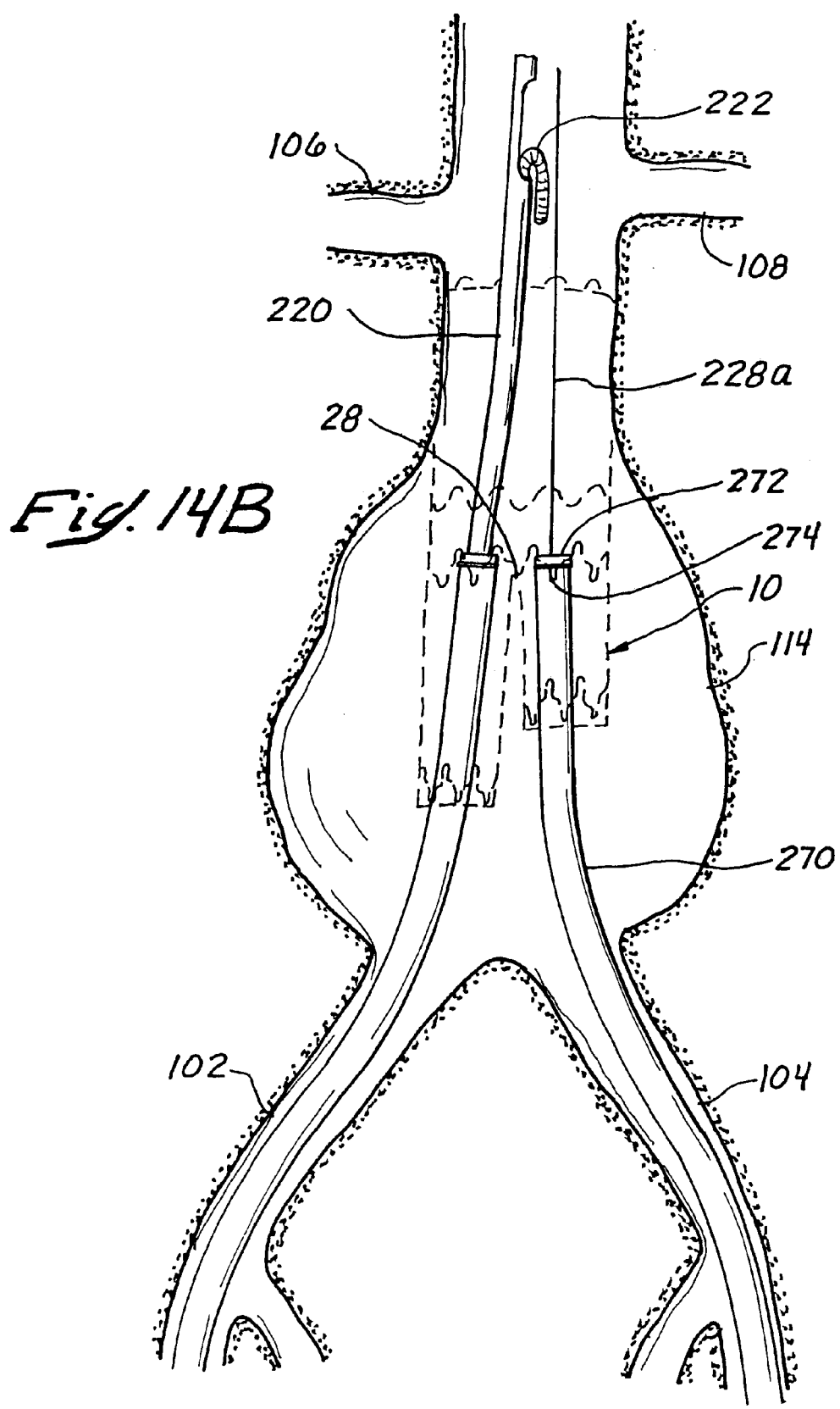
FIG. 14B is a sectional aneurysmic view with a second introducer sheath positioned at the septum region and the dilator removed therefrom.

As illustrated in FIGS. 14A and 14B, a second introducer assembly 230 is introduced with the help of a dilator 240 over the stiff guidewire 228a in the manner previously described for the first introducer assembly 130. The dilator 240 is removed leaving a second sheath 270 in position with its distal tip 272 adjacent the graft septum region 28. Again, a radiopaque marker 274 on the distal tip 272 aligns with the septum region 28 and its radiopaque markers 84, 85 (FIG. 1).

Figure 15A:
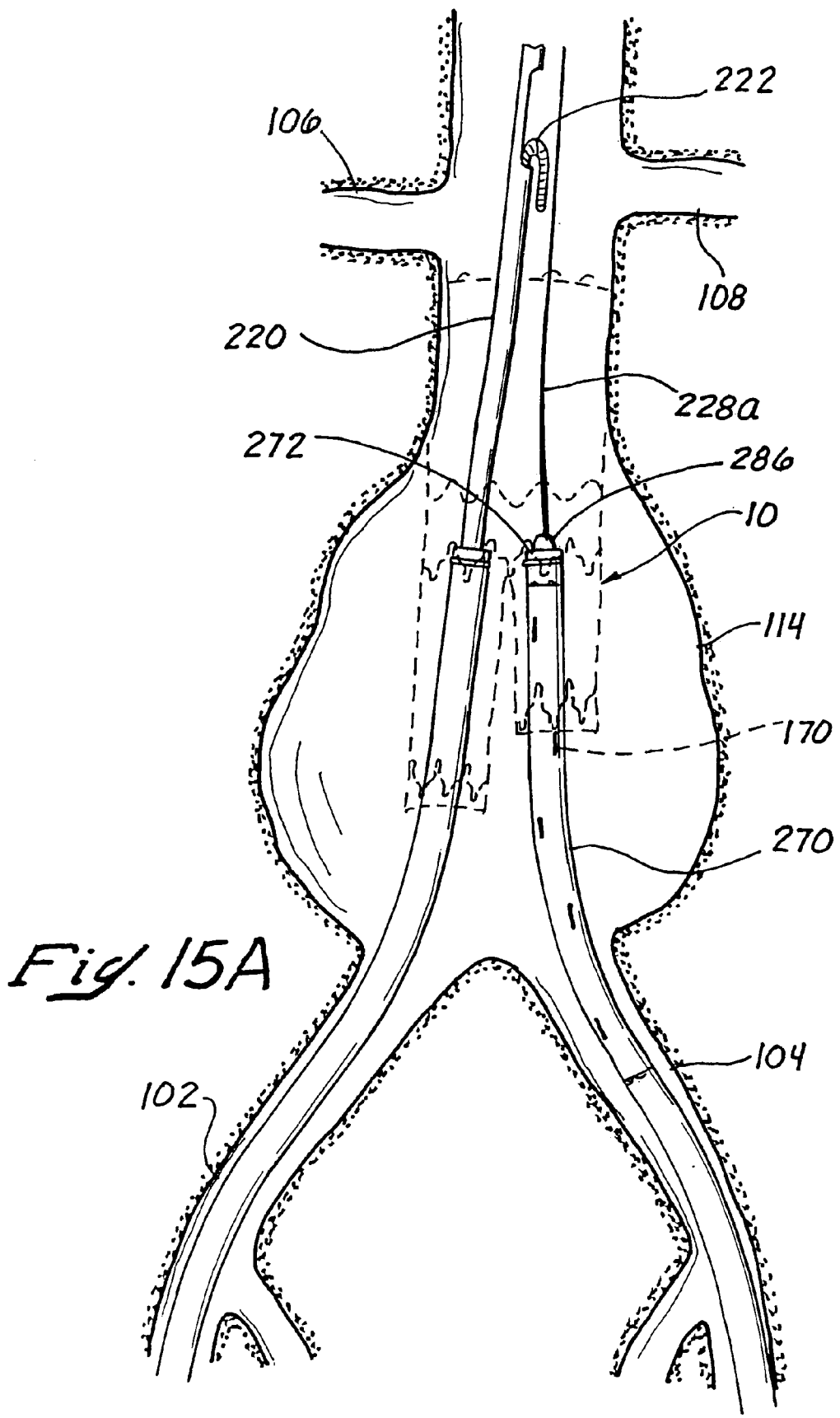
FIG. 15A is a sectional aneurysmic view of a balloon of the second catheter assembly and an associated first extension graft advanced within the second introducer sheath to the septum region.

As seen in FIG. 15A, a second catheter assembly, on which is packaged the tubular graft extension 170' is then introduced through the sheath 270. A pusher body, (not shown but similar to that described above) pushes the tubular graft extension 170 distally within the sheath 270. Again, this procedure for advancing a graft upstream with respect to the aneurysm 114 while housed within the sheath 270 is necessary to avoid difficulties associated with displacing an irregularly shaped object against the blood flow. It is especially significant given that the trunk portion 12 has been expanded into contact with the abdominal aorta 100, and thus the entire blood flow through the abdominal aorta continues through the graft legs 14, 16. Ultimately, a distal portion 286 of the inflation balloon extends from the distal tip 272 of sheath 270.

Figure 15B:
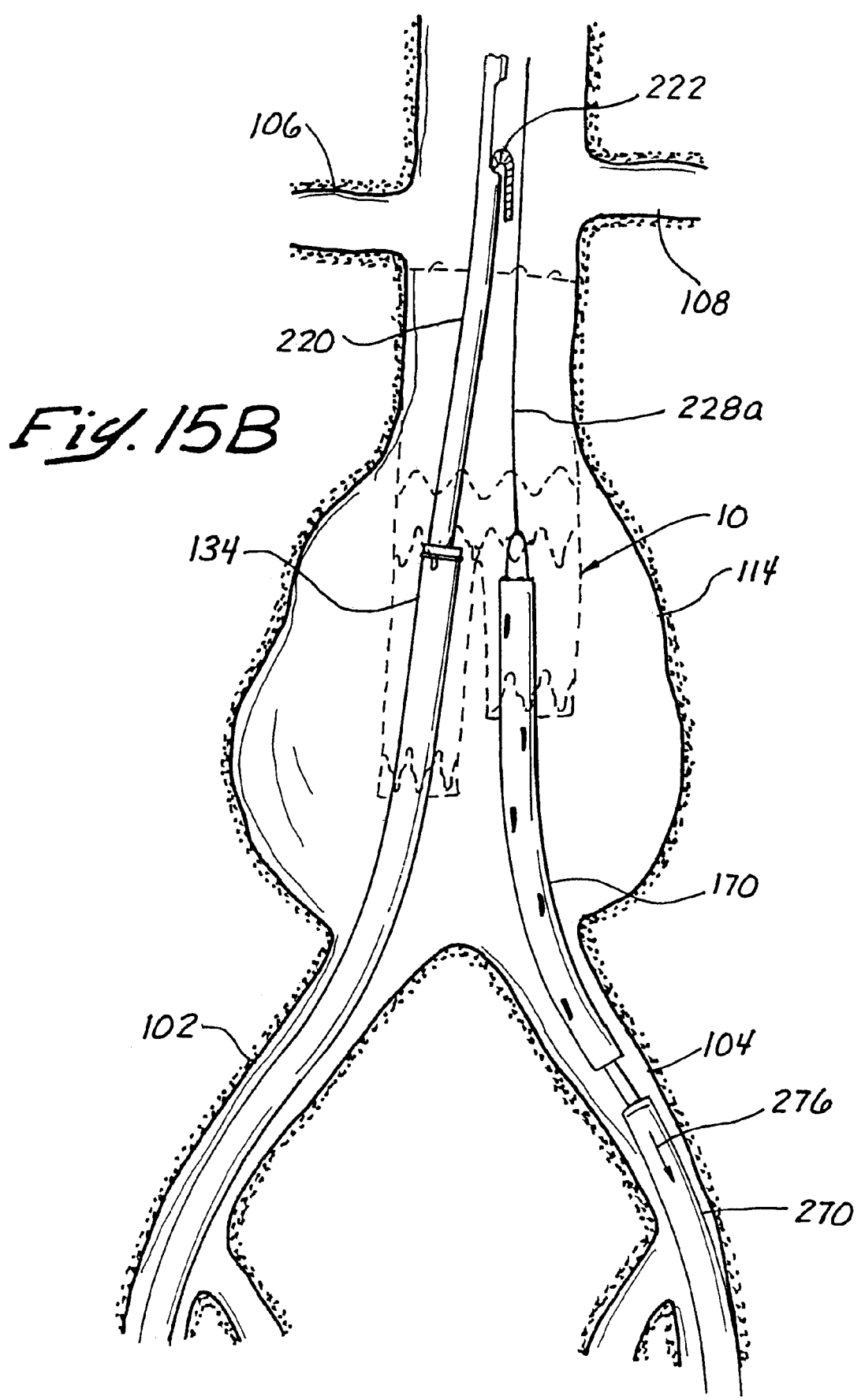
FIG. 15B is a sectional aneurysmic view with the second introducer sheath withdrawn to a position downstream of the now exposed first extension graft.

Once the tubular graft extension 170 is in place, the second introducer sheath 270 is withdrawn (as seen by the arrow 276 in FIG. 15B) to a position within the left common iliac artery 104. After displacing the second introducer sheath 270, the pusher body is retracted slightly to release the proximal end of the graft extension 170. FIG. 15B illustrates the compressed balloon-expandable tubular graft extension 170 in proper position for expansion and implantation.

Figure 15C:
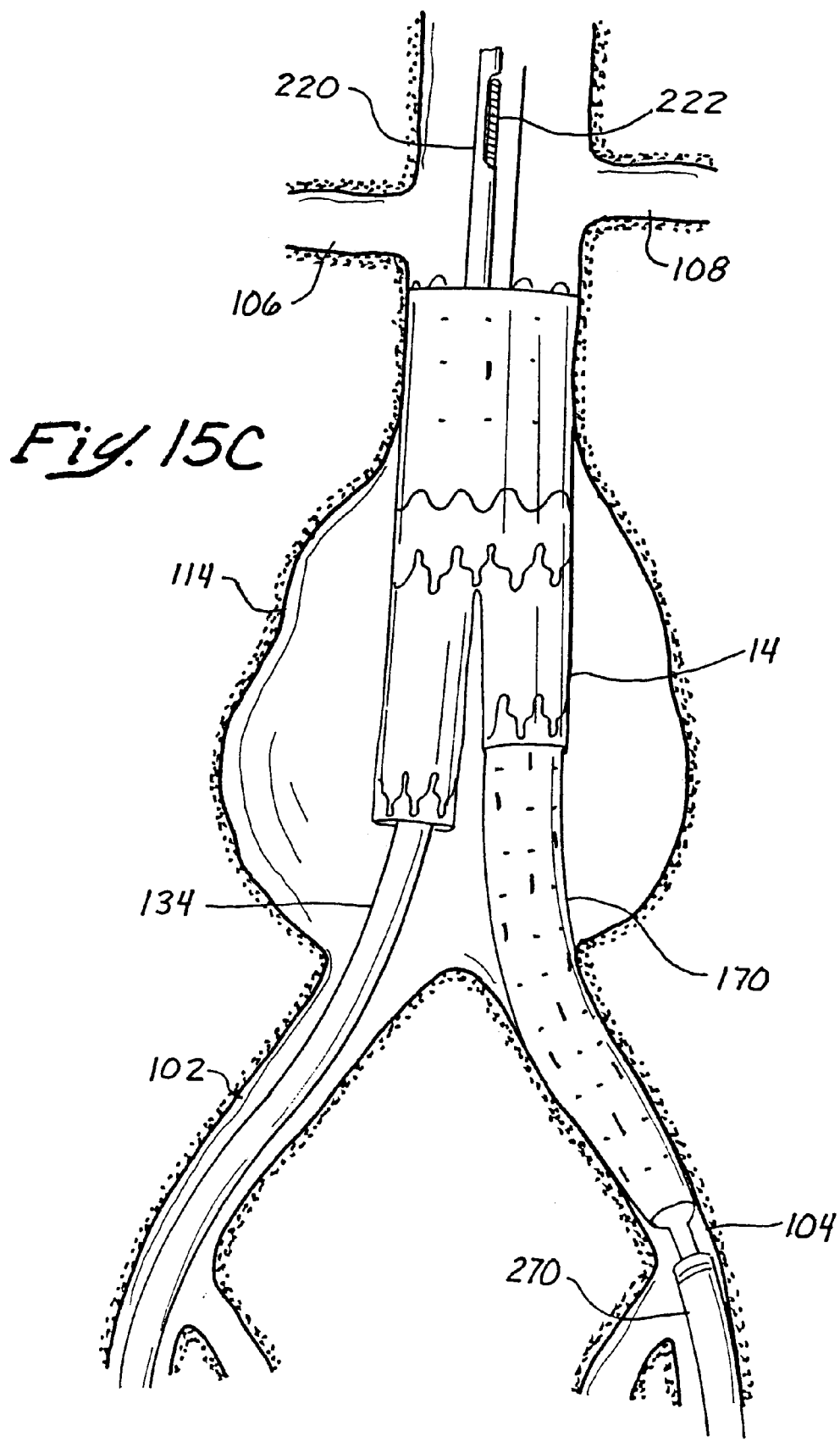
FIG. 15C is a sectional aneurysmic view with the first extension graft from FIG. 15B being expanded from inflation of the balloon on the second catheter assembly.

As illustrated in FIG. 15C, the balloon on the second catheter assembly is then inflated forcing the upstream portion of the graft extension 170 into contact with the inner surface of the contralateral leg 14, and downstream portion of the graft extension into contact with the inner surface of the left common iliac artery 104. As with the inflation balloon 194 for the trunk portion 12 the inflation balloon for the tubular graft extension 170 is first deflated and then stretched to remove it from within graft without snagging.

After the tubular graft extension 170 on the contralateral side has been expanded, the directional catheter 220 in the first introducer sheath 134 is withdrawn. First, however, the spring portion 222 is straightened to its home position (FIG. 15C) to enable the catheter 220 to be retracted within the sheath 134.

As seen in FIG. 16A, a third catheter assembly on which is packaged another tubular graft extension 170' is then advanced over the primary guidewire 128 and through the lumen of the sheath 134 until a distal end 296 of the inflation balloon projects slightly from the distal tip 138. Again, a radiopaque marker on the distal end of the balloon catheter is used to place it in registry with the marker 139 on the distal tip 138, which was previously registered with the marker at the graft septum region 28.

The first introducer sheath 134 is slightly larger than the second sheath 270 because it is sized for passage of the balloon 194 of the first catheter assembly on which the trunk portion 12 is wrapped. For example, the inner diameter of the introducer sheath 134 may be 19 French, while the inner diameter of the second sheath 270 may be 16 French. As a result, there is some acceptable clearance between passage of the third catheter assembly and tubular graft extension 170' thereon and the inner lumen of the introducer sheath 134. In this manner the introducer sheath 134 need not be removed and replaced with a smaller one.

Figure 16D:
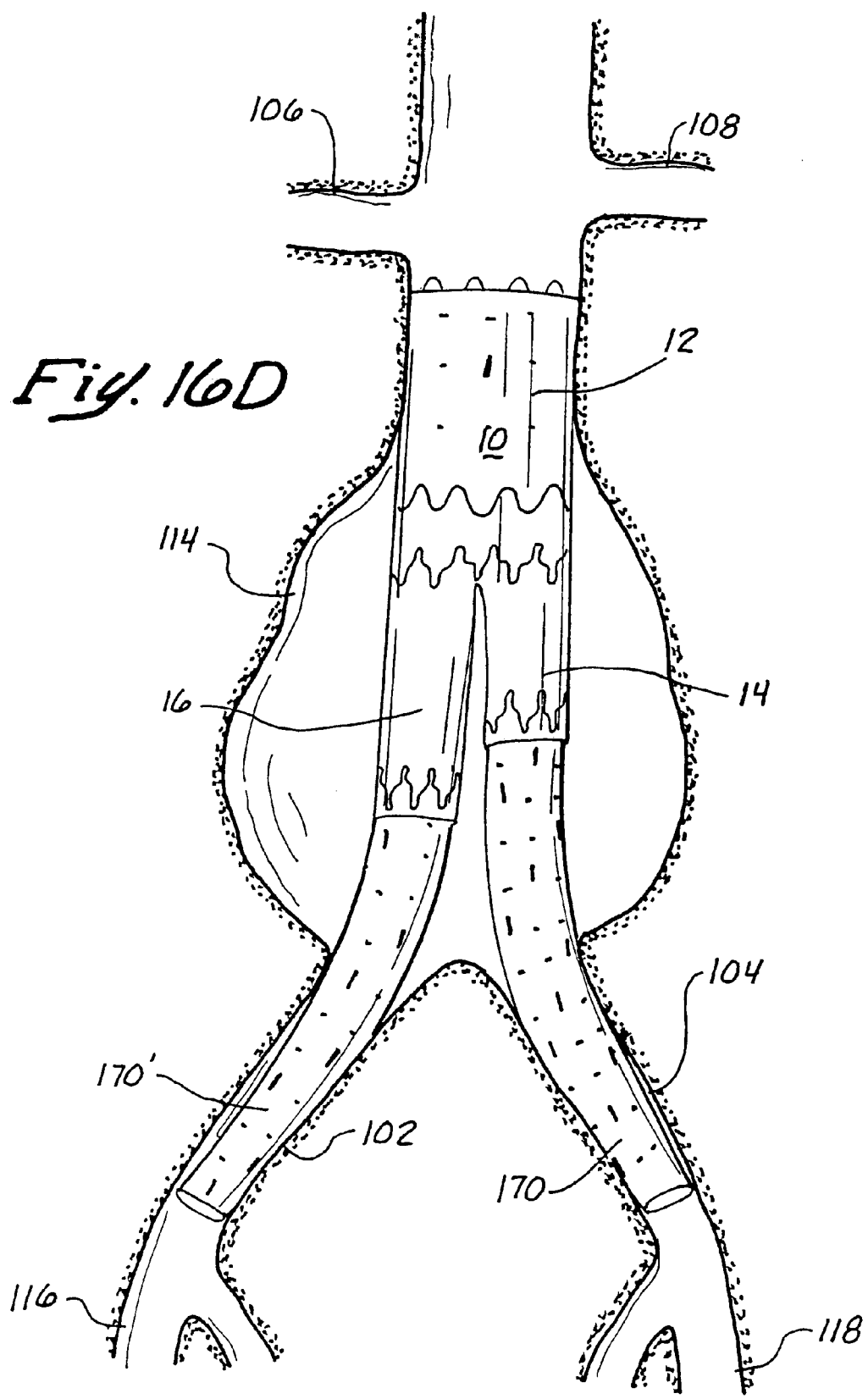
FIG. 16D is a sectional aneurysmic view with a fully deployed aortic graft and first and second graft extensions.

In the same manner as on the contralateral side, and as illustrated in FIG. 16B, first the sheath 134 and then the pusher body (not shown) are withdrawn proximally to release the tubular graft extension 170' such that its upstream end is inside the ipsilateral leg 16 of the aortic graft 10 and its downstream end is within the right common iliac artery 102. The catheter balloon is inflated to force the upstream end of the graft extension 170' into contact with the inner surface of the ipsalateral leg 16. At the same time, the balloon forces the downstream end of the graft extension 170' into contact with the inner surface of the right common iliac artery 102. The final expanded position of the tubular graft extension 170' is seen in FIG. 16D.

FIG. 16C illustrates a cross-section of the left common iliac artery 104 with the first tubular graft extension 170 expanded into contact therewith. As was described with respect to FIG. 2A, the wireforms 176 terminate in ends which are secured outside the extension wall 175 with crimps 178. The crimps 178 as shown project outward from the wall 175 at a slight angle and provide additional friction to locate the extension 170 within the artery 104. Advantageously, the crimps 178 are not sharp and do not penetrate the vessel wall, as with some prior art grafts. Instead, the irregular surface formed by the multiple crimps 178 prevents migration of the tubular graft extension 170 without damage to the wall of the artery 104.

Subsequently, the inflation balloon is deflated and then stretched before removing it along with the third catheter assembly from within the graft extension 170'.

In one embodiment of the present invention, the upstream portions of either of the graft extensions 170, 170' may be slightly over-sized to maximize the frictional engagement with the downstream portions of the respective contralateral or ipsilateral legs 14, 16. In particular, the over-expansion of the balloon-expandable wireforms slightly beyond the diameter of the distal self-expandable wireforms causes the distal self-expandable wireforms of the contralateral or ipsilateral legs to exert a radially inward force against the balloon-expandable portions of the graft extension. This resistance serves to improve the frictional engagement between the contralateral downstream leg and the graft extension. Furthermore, the respective wireforms and associated crimps tend to hook together to more securely couple the graft extensions 170, 170' to the respective contralateral or ipsilateral legs 14, 16.

In an alternate embodiment, colloquially known as the "kissing" technique, both the ipsilateral and contralateral balloon catheters could remain in place during implantation of both leg extensions 170, 170'. In this technique, the third catheter balloon for the ipsalateral leg extension 170' is inflated while the second catheter balloon remains within the contralateral leg extension 170. In other words, while the third catheter balloon inflates, the second catheter balloon remains in place in the contralateral leg extension 170, and is preferably deflated to ambient pressure but is not stretched or reduced by a vacuum. The third catheter balloon is subsequently deflated, stretched and removed, followed by deflation, stretching and removal of the second catheter balloon. The use of the kissing technique or the more common sequential contralateral-ipsalateral extension implantation technique is up to the preference of the surgeon.

An angiographic examination may take place to determine if the grafts are correctly placed and functioning. The second sheath assembly and the stiff guidewires are withdrawn and the contralateral incision or puncture is sutured. The first introducer sheath assembly is then withdrawn and the right femoral incision is sutured. The result is a functioning trouser graft bridging an aneurysm as illustrated in FIG. 16D.

The operation may be carried out using a general anaesthetic, an epidural anaesthetic, or in suitable cases, using only a local anaesthetic.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An assembly of tubular prostheses, comprising:
   a first tubular prosthesis including a graft body and at least one self-expanding wireform, the first tubular prosthesis terminating at a downstream end in an open mouth; and
   a second tubular prosthesis including a graft body and at least one balloon-expandable wireform, the second tubular prosthesis terminating at an upstream end positionable within the open mouth of the first tubular prosthesis, the second tubular prosthesis being expandable into contact with the first tubular prosthesis and expandable sufficiently farther to outwardly stress the self-expanding wireform in the first tubular prosthesis and produce an inward compressive force on the upstream end of the second tubular prosthesis.

2. The intraluminal prosthesis of claim 1, wherein the balloon-expandable wireform is woven through and has a crimp positioned external to the graft body of the second tubular prosthesis, the crimp being positionable to interlock with the self-expanding wireform on the first tubular prosthesis.

3. The intraluminal prosthesis of claim 2, wherein the second tubular prosthesis includes a plurality of the balloon-expandable wireforms generally evenly spaced therealong, each of the wireforms having a crimp positioned external to the graft body of the second tubular prosthesis, some of which are fractionally engageable with a surrounding body lumen.

4. The intraluminal prosthesis of claim 1, wherein the at least one self-expanding wireform comprises a curvilinear configuration having loops which define crests and valleys.

5. The intraluminal prosthesis of claim 4, wherein the self-expanding wireform further comprises intermediate sections between the crests and valleys having an "S" shape along their length.

6. The intraluminal prosthesis of claim 1, wherein the at least one balloon-expandable wireform is woven into the trouser graft but positioned primarily on the interior surface of the graft body at the trunk.

7. The intraluminal prosthesis of claim 1, wherein the at least one balloon-expandable wireform is configured with a plurality of intermediate segments which are connected by corresponding crests and valleys and the intermediate segments are positioned at an angle with respect to each other of greater than about ninety degrees.

8. The intraluminal prosthesis of claim 7, wherein the intermediate segments are positioned at an angle with respect to each other within a range of about one hundred to about one hundred thirty-five degrees.

9. The intraluminal prosthesis of claim 8, wherein the intermediate segments are positioned at an angle with respect to each other within a range of about one hundred twenty to about one hundred twenty-five degrees.

10. The intraluminal prosthesis of claim 1, wherein the first tubular prosthesis includes a graft body having a first self-expanding wireform at an upstream end and a second self-expanding wireform at a downstream end and the first tubular prosthesis further includes a lateral reinforcement wire coupled to the first tubular prosthesis between the first self-expanding wireform and the second self-expanding wireform.

11. The intraluminal prosthesis of claim 10, wherein the lateral reinforcement wire is attached to the exterior of the graft body.

12. The intraluminal prosthesis of claim 11, wherein the first and second self-expanding wireforms each have alternating peaks and valleys around their respective circumferences, and wherein the lateral reinforcement wire extends between a valley on one of the self-expanding wireforms and a peak on the other of the self-expanding wireforms.

13. The intraluminal prosthesis of claim 1, wherein the first tubular prosthesis comprises a balloon-expandable wireform at a first, upstream end and the self-expanding wireform is positioned at the second, downstream end.

14. The intraluminal prosthesis of claim 1, wherein the balloon-expandable wireform is located at the upstream end of the second tubular prosthesis.

15. The intraluminal prosthesis of claim 1, wherein the self-expanding wireform provides the first tubular prosthesis with expandability and the at least one balloon-expandable wireform provides the second tubular prosthesis with expandability, and wherein the expanded second tubular prosthesis is attachable to the downstream end of the expanded first tubular prosthesis by being over-sized with respect to the first tubular prosthesis to induce the inward compressive force exerted by the first tubular prosthesis.

16. The intraluminal prosthesis of claim 1 wherein the initial expanded diameter of the at least one self-expanding wireform is slightly larger than the diameter of the portion of the graft body to which it is attached.

17. The intraluminal prosthesis of claim 1 wherein the self-expanding wireform is located at the downstream end of the first tubular prosthesis.

18. The intraluminal prosthesis of claim 1 wherein the first tubular prosthesis is a bifurcated trunk graft terminating in a downstream end having two trunk legs and wherein at least one of the two trunk legs terminates at a downstream end in an open mouth.

19. The intraluminal prosthesis of claim 18 wherein the self-expanding wireform is located at the downstream end of the at least one of the two trunk legs.

20. An assembly of tubular prostheses, comprising:
   a first tubular prosthesis including a graft body having an upstream end and terminating at a downstream end in an open mouth and comprising at least one balloon-expandable wireform located at the upstream end and at least one self-expanding wireform located at the downstream end; and
   a second tubular prosthesis including a graft body having an upstream end and a downstream end and comprising at least one balloon-expandable wireform at the upstream end and at least one balloon-expandable wireform at the downstream end, the upstream end of the second tubular prosthesis positionable within the open mouth of the first tubular prosthesis, the second tubular prosthesis being expandable into contact with the first tubular prosthesis and expandable sufficiently farther to outwardly stress the self-expanding wireform in the first tubular prosthesis and produce an inward compressive force on the upstream end of the second tubular prosthesis.

21. An assembly of tubular prostheses, comprising:

a first tubular prosthesis including a graft body and at least one self-expanding wireform, the first tubular prosthesis terminating at a downstream end in an open mouth; and a second tubular prosthesis including a graft body and at least one balloon-expandable wireform woven through the graft body and having a crimp positioned external to the graft body, the second tubular prosthesis terminating at an upstream end positionable within the open mouth of the first tubular prosthesis, the second tubular prosthesis being expandable into contact with the first tubular prosthesis and expandable sufficiently farther to outwardly stress the self-expanding wireform in the first tubular prosthesis and produce an inward compressive force on the upstream end of the second tubular prosthesis;

wherein the crimp positioned on the outside of the graft body of the second tubular prosthesis is positionable to interlock with the self-expanding wireform on the first tubular prosthesis.

22. A method of deploying an assembly of tubular prostheses to a site of implantation, comprising:

endoluminally delivering a first tubular prosthesis having one or more self-expanding wireforms to a site of implantation, a first end of the first tubular prosthesis being positioned within a first vessel portion and a second end of the first tubular prosthesis being open;

delivering a second tubular prosthesis having one or more balloon-expandable wireforms into position with one end of the second tubular prosthesis being inserted within the open end of the first tubular prosthesis and with the other end of the second tubular prosthesis being placed within a second vessel portion; and expanding the first end of the second tubular extension with a balloon catheter into contact with the second tubular prosthesis, the first tubular prosthesis thereby being expanded beyond a relaxed state so that it imparts an inward compressive force on the second tubular prosthesis.

23. The method of claim 22 further comprising the step of expanding the second end of the second tubular extension with a balloon catheter into contact with the second vessel portion.

24. The method of claim 22 wherein the first tubular prosthesis has one or more balloon expandable wireforms at the first end and the first end of the tubular prosthesis is attached to the first vessel portion by expanding the first end of the tubular prosthesis with a balloon catheter.

25. A method of deploying an assembly of tubular prostheses to a site of implantation, comprising:

endoluminally delivering a first tubular prosthesis having one or more balloon expandable wireforms at the first end and one or more self-expanding wireforms at a second end to a site of implantation;

attaching the first end of the tubular prosthesis to a first vessel portion by expanding the first end of the tubular prosthesis with a balloon catheter and permitting the one or more self-expanding wireforms to open the second end of the first tubular prosthesis;

delivering a second tubular prosthesis having one or more balloon-expandable wireforms into position with one end of the second tubular prosthesis being inserted within the open end of the first tubular prosthesis and with the other end of the second tubular prosthesis being placed within a second-vessel portion; and expanding the first end of the second tubular extension with a balloon catheter into contact with the second tubular prosthesis, the first tubular prosthesis thereby being expanded bee on the second tubular prosthesis.

* * * * *

UNITED STATES PATENT AND TRADEMARK OFFICE
CERTIFICATE OF CORRECTION

PATENT NO.  : 6,375,675 B2
DATED       : April 23, 2002
INVENTOR(S) : Mark Dehdashtian, Geoffrey H. White and Weiyun Yu It is certified that error appears in the above-identified patent and that said Letters Patent is hereby corrected as shown below:

Column 1,
Line 54, please delete "the-se" and insert -- these. --

Column 4,
Line 35, after "portion" please delete "is; deflected" and insert -- is deflected. --

Column 5,
Line 6, after "assembly" please delete "is; deployed" and insert -- is deployed. --

Column 6,
Line 13, after "balloon shown exposed" please delete "arid" and insert -- and. --
Line 33, after "FIG. 10A" please delete "is, a" and insert -- is a. --

Column 8,
Line 17, after "renal arteries 106," please delete "100" and insert -- 108. --
Line 66, after "sheath 143 and" please delete "during, any" and insert -- during any. --

Column 9,
Line 33, after "upstream" please delete "of, one" and insert -- of one. --

Column 19,
Line 50, after "pusher body" please delete "134" and insert -- 184. --

Column 25,
Line 16, after "thereby further" please delete "reducing, the" and insert -- reducing the. --

Column 29,
Line 39, after "which are" please delete "fractionally" and insert -- frictionally. --

UNITED STATES PATENT AND TRADEMARK OFFICE
CERTIFICATE OF CORRECTION

PATENT NO. : 6,375,675 B2
DATED : April 23, 2002
INVENTOR(S) : Mark Dehdashtian, Geoffrey H. White and Weiyun Yu It is certified that error appears in the above-identified patent and that said Letters Patent is hereby corrected as shown below:

<u>Column 32,</u>
Line 35, after "being expanded" please delete "bee" and insert -- beyond a relaxed state so that it imparts an inward compressive force. --

Signed and Sealed this

Ninth Day of November, 2004

JON W. DUDAS
*Director of the United States Patent and Trademark Office*